United States Patent [19]

Funaki et al.

[11] Patent Number: 4,749,716
[45] Date of Patent: Jun. 7, 1988

[54] GEOMETRICAL ISOMER OF 1-SUBSTITUTED-1-TRIAZOLYSTYRENES

[75] Inventors: Yuji Funaki; Hirofumi Oshita, both of Toyonaka; Shigeo Yamamoto, Ikeda; Shizuya Tanaka, Minoo; Toshiro Kato, Takarazuka, all of Japan

[73] Assignee: Sumitomo Chemical Company, Limited, Osaka, Japan

[21] Appl. No.: 772,429

[22] Filed: Sep. 4, 1985

Related U.S. Application Data

[62] Division of Ser. No. 130,108, Mar. 13, 1980.

[30] Foreign Application Priority Data

| Mar. 20, 1979 | [JP] | Japan | 54-32876 |
| Apr. 5, 1979 | [JP] | Japan | 54-41659 |
| Aug. 6, 1979 | [JP] | Japan | 54-100547 |
| Sep. 10, 1979 | [JP] | Japan | 54-116576 |
| Sep. 21, 1979 | [JP] | Japan | 54-122366 |
| Sep. 25, 1979 | [JP] | Japan | 54-123485 |
| Sep. 26, 1979 | [JP] | Japan | 54-124571 |
| Jan. 30, 1980 | [JP] | Japan | 55-10568 |

[51] Int. Cl.$^4$ .................. A01N 43/653; C07D 249/08
[52] U.S. Cl. ..................... 514/383; 548/262; 71/76; 71/92
[58] Field of Search ............... 548/262; 71/76, 92, 71/118, 123; 514/383

[56] References Cited

U.S. PATENT DOCUMENTS

| 3,277,171 | 10/1966 | Hopkins | 71/118 |
| 3,830,642 | 8/1974 | Moon | 71/123 |
| 3,912,752 | 10/1975 | Meiser et al. | 548/262 |
| 4,079,143 | 3/1978 | Balasubramanyan et al. | 548/262 |
| 4,086,351 | 4/1978 | Balasubramanyan et al. | 548/262 |
| 4,182,862 | 1/1980 | Chan | 548/262 |

*Primary Examiner*—Glennon H. Hollran
*Assistant Examiner*—Patricia L. Morris
*Attorney, Agent, or Firm*—Stevens, Davis, Miller & Mosher

[57] ABSTRACT

The present invention relates to one of the two geometrical isomers (a compound defined as I-A isomer in the description below) of a triazole compound represented by the formula (I) or (II),

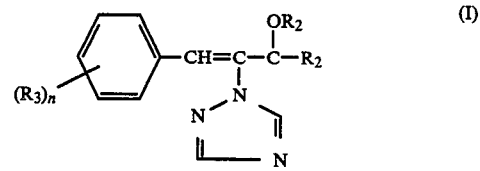

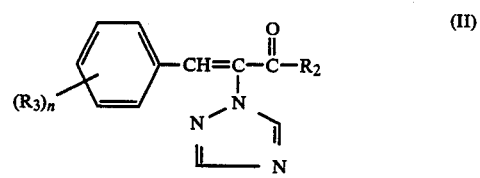

wherein $R_1$ is a hydrogen atom, a $C_1$–$C_4$ alkyl, $C_3$–$C_4$ alkenyl or 2-propynyl group, $R_2$ is a $C_1$–$C_6$ alkyl, cyclopropyl or 1-methylcyclopropyl group, $R_3$, which may be the same or different, is a halogen atom, a $C_1$–$C_4$ alkyl, halogen-substituted $C_1$–$C_3$ alkyl, $C_1$–$C_4$ alkoxy, phenoxy, phenyl, cyano or nitro group, n is an integer of 0 to 3, and the term, halogen, means chlorine, bromine and fluorine atoms, its salts, production thereof and a fungicide, herbicide and/or plant growth regulator for agriculture and horticulture containing said compound as an active ingredient.

3 Claims, No Drawings

GEOMETRICAL ISOMER OF 1-SUBSTITUTED-1-TRIAZOLYSTYRENES

RELATED PATENTS

This application is a divisional application of U.S. Ser. No. 130,108 filed Mar. 13, 1980, now U.S. Pat. No. 4,554,007.

The present invention relates to one of the two geometrical isomers (a compound defined as I-A isomer in the description below) of a triazole compound represented by the formula (I),

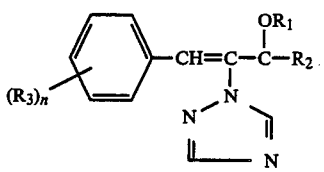

wherein $R_1$ is a hydrogen atom, a $C_1$-$C_4$ alkyl, $C_3$-$C_4$ alkenyl or 2-propynyl group, $R_2$ is a $C_1$-$C_6$ alkyl, cyclopropyl or 1-methylcyclopropyl group, $R_3$, which may be the same or different, is a halogen atom, a $C_1$-$C_4$ alkyl, halogen-substituted $C_1$-$C_3$ alkyl, $C_1$-$C_4$ alkoxy, phenoxy, phenyl, cyano or nitro group, n is an integer of 0 to 3, and the term, halogen, means chlorine, bromine and fluorine atoms, its salts. The invention also relates to fungicides herbicides and/or plant growth regulator for agriculture and horticulture containing the subject compound as an active ingredient.

Every triazole compound of the formula (I) has two geometrical isomeric forms, the Z-form and the E-form, represented by the formulae,

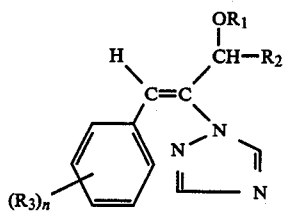

Z-form

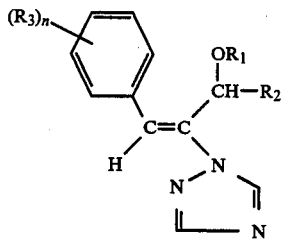

E-form

It is not clear at present which of the two isomeric forms the compounds of the present invention belong to, and therefore the properties of the compounds can only be expressed conditionally. These two isomers can be distinguished from each other by melting point, NMR spectrum or gas chromatography, but the difference between them can be characterized more generally and clearly by the starting material used to produce the compounds i.e., a triazole compound of the formula (II),

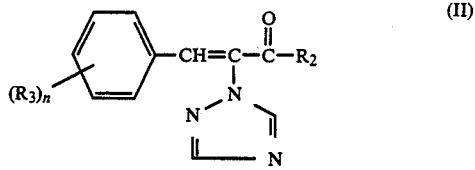

wherein $R_2$, $R_3$ and n are as defined above.

The triazole compound of the formula (I) is obtained by reducing a triazole compound of the formula (II) to obtain a triazole compound of the formula (I) in which $R_1$ is a hydrogen atom and then subjecting the product thereof to etherification. The scheme is represented as follows:

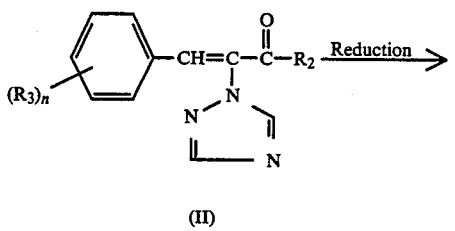

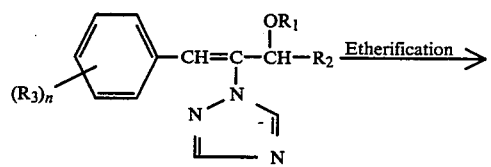

(I) ($R_1$ = H)

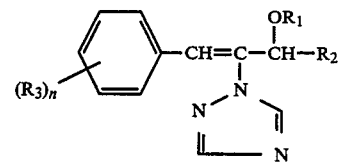

(I) ($R_1$: Substituents other than H)

wherein $R_1$, $R_2$, $R_3$ and n are as defined above.

Hereupon, one of the two geometrical isomers of the triazole compound (II), of which the olefin proton appears at a higher magnetic field on the NMR spectrum in deutero chloroform, is defined as II-A isomer, and the other, of which the olefin proton appears at a lower magnetic field on the NMR spectrum in deutero chloroform, is defined as II-B isomer.

Further, the compound (I) in which $R_1$ is a hydrogen atom, produced by reducing II-A isomer, is defined as I'-A isomer; the compound (I) in which $R_1$ is a defined substituent other than a hydrogen atom, produced by etherifying I'-A isomer, is defined as I''-A isomer; and I'-A isomer and I''-A isomer are defined generically as I-A isomer. The corresponding compounds derived from II-B isomer in the same manner as above are defined as I'-B isomer, I''-B isomer and I-B isomer, respectively. The present invention relates to I-A isomer and II-A isomer which is an intermediate for I-A isomer.

Hitherto, there has been developed a large number of organosynthetic compounds which have made great contributions as agricultural chemicals in sustaining and increasing the stable supply of agricultural and horticultural crops by their activity against diseases and pests doing damage to the crops. It is, however, a fact that many problems still exist. Such problems are sometimes solved, for example, by the development of new and more desirable pesticides, or they are also solved by investigating and improving procedures for applying the conventional pesticides.

There are many organosynthetic compounds which exist in the form of geometrical or optical isomers. In fact, there are many cases in which pesticides containing these isomers are in practical use as agricultural chemicals. It is well known, not only in agricultural chemicals but also in many other fields that, many of active ingredients having the isomeric forms, show differences in biological activity between the isomers. Recently, the problem of environmental pollution has become very serious in the field of agriculture and horticulture, and it is important to reduce this problem by using one of a pair of isomers which is stronger in activity. Also, this may be considered as bringing about a more economical effect in the production of the compound as well as in the practical application as agricultural chemicals. From this standpoint, therefore, it may be considered as contributing to this field to provide the isomer having a stronger activity.

From this viewpoint, the inventors made a further study on the compounds already found by the inventors [Published Unexamined Japanese Patent Application No. 130661/1978, Belgian Pat. No. 870243 (Published Unexamined Japanese Patent Application No. 41875/1979)]. As a result, it was found that the present compounds defined as I-A isomer, one of the two geometrical isomers of a triazole compound represented by the formula (I), have a higher fungicidal activity on a wider range of plant pathogens as well as a higher herbicidal effect and a higher plant growth regulating action than the compounds defined as I-B isomer, in other words, they have excellent properties as agricultural chemicals.

There are many other well-known triazole compounds disclosed in British Pat. No. 1364619, Belgian Pat. No. 845433, West German Pat. Nos. 2610022, 2654890 and 2734426, and U.S. Pat. No. 4,086,351. But, the characteristics of the present invention which distinguish the claimed invention over the prior art is that the following new information was found: One of the two geometrical isomers of the triazole compound (I) characterized by having (1) a double bond (benzylidene group) and (2) a hydroxy group or its ethers in its structure,

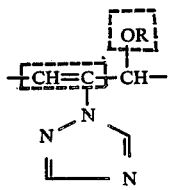

has far superior properties as agricultural chemicals as compared with the other geometrical isomer. In this point, the present compounds have a different structural characteristic from that of the foregoing well-known compounds, and besides they haave far superior properties as compared with the well-known compounds. Consequently, the originality of the present invention is such a one as to be never imaginable from the prior art.

As diseases on which the compounds of the present invention (I-A isomer) can exert an excellent protective activity, there may be given rice blast (*Pyricularia oryzae*), sheath blight of rice (*Pellicularia sasakii*), canker of apple (*Valsa mali*), blossom blight of apple (*Sclerotinia mali*), powdery mildew of apple (*Podosphaera leucotricha*), apple scab (*Venturia inaequalis*), fruit spot of apple (*Mycosphaerella pomi*), alternaria leaf spot of apple (*Alternaria mali*), black spot of pear (*Alternaria kikuchiana*), powdery mildew of pear (*Phyllactinia pyri*), rust of pear (*Gymnosporangium haraeanum*), scab of pear (*Venturia nashicola*), melanose of citrus (*Diaporthe citri*), citrus scab (*Elsinoe fawcetti*), common green mold of citrus fruit (*Penicillium digitatum*), blue mode of orange (*Penicillium italicum*), brown rot of peach (*Sclerotinia cinerea*), anthracnose of grape (*Elsinoe ampelina*), ripe rot of grape (*Glomerella cingulata*), gray mold of grape (*Botrytis cinerea*), powdery mildew of grape (*Uncinula necator*), rust of grape (*Phakopsora ampelopsidis*), crown rust of oats (*Puccinia coronata*), powdery mildew of barley (*Erysiphe graminis*), leaf blotch of barley (*Rhynchosporium secalis*), stripe of barley (*Helminthosporium gramineum*), loose smut of barley (*Ustilago nuda*), covered smut of barley (*Ustilago hordei*), typhula snow blight of barley (*Typhula incarnata*), stem rust of barley (*Puccinia graminis*), leaf rust of wheat (*Puccinia recondita*), loose smut of wheat (*Ustilago tritici*), bunt of wheat (*Tilletia caries*), speckled leaf blotch of wheat (*Septoria tritici*), glume blotch of wheat (*Septoria nodorum*), yellow rust of wheat (*Puccinia striiformis*), stem rust of wheat (*Puccinia graminis*), powdery mildew of wheat (*Erysiphe graminis*), powdery mildew of cucumber (*Sphaerotheca fuliginea*), gray mold of cucumber (*Botrytis cinerea*), gummy stem blight of cucumber (*Mycosphaerella melonis*), sclerotinia rot of cucumber (*Sclerotinia sclerotiorum*), anthracnose of cucumber (*Colletotrichum lagenarium*), leaf mold of tomato (*Cladosporium fulvum*), powdery mildew of tomato (*Erysiphe cichoracearum*), early blight of tomato (*Alternaria solani*), gray mold of eggplant (*Botrytis cinerea*), verticillium wilt of eggplant (*Verticillium albo-atrum*), powdery mildew of eggplant (*Erysiphe cichoracearum*), powdery mildew of pimento (*Leveillula taurica*), gray mold of strawberry (*Botrytis cinerea*), powdery mildew of strawberry (*Sphaerotheca humuli*), brown spot of tobacco (*Alternaria longipes*), powdery mildew of tobacco (*Erysiphe cichoracearum*), cercospora leaf spot of beet (*Cercospora beticola*), leaf spot of peanut (*Cercospora personata*), brown leaf spot of peanut (*Cercospora arachidicola*) and the like.

By further study on the antimicrobial activity of the present compounds, I-A isomer, it became clear that the present compounds exhibit also an antimicrobial activity against Trichophyton rubrum. Thus, it was found that there is a possibility of the present compounds being usable as an antimycotic for medical purposes.

Further, the compounds of the present invention, I-A isomer, can also be used as a plant growth regulator, acting to control the growth of useful plants. For example, they can be used for preventing the spindly growth of rice, wheat, turf, trees for hedge and fruit trees and for dwarfing horticultural plants such as potted chrysanthemum.

In the cultivation of rice and wheat, lodging of rice and wheat caused by the application of more fertilizer than required or strong wind becomes often serious. But the application of the present compounds at a proper time is effective for controlling the height of rice and wheat and preventing lodging.

In the cultivation of potted chrysanthemum, the application of the present compounds is useful to elevate the commercial value of the chrysanthemum because they can shorten the height of the stem with no adverse effect on the flower.

The compounds of the present I-A isomer, invention have a strong herbicidal activity against grassy field weeds such as barnyard grass (*Echinochloa crus-galli*), large crabgrass (*Digitaria sanguinalis*) and green foxtail (*Setaria viridis*); broad-leaved field weeds such as Umbrella plant (*Cyperus difformis* L.), redroot pigweed (*Amaranthus retroflexus*), common lambsquarter (*Chenopodium album*), common purslane (*Portulaca oleracea*) and chickweed (*Stellaria media*); and annual weeds and perennial weeds in paddy field such as barnyard grass (*Echinochloa crus-galli*), pickerel weed (*Monochoria viaginalis*), toothcup (*Rotala indica* Koehne), *Dopatrium junceum*, Bulrush sp. (*Scirpus juncoides* var. Hotarui Ohwi) and slender spikerush (*Eleocharis acicularis*).

When the compounds of the present invention are applied to fields, they are also very superior in the following points: They have a strong herbicidal activity against main weeds in fields; they show the activity by either of soil treatment before the germination of weeds or foliage treatment at the beginning of growth; and besides they can be applied safely without doing damage to main crops (e.g. rice, soybean, cotton, corn, peanut, sunflower, beet) as well as vegetables (e.g. lettuce, radish, tomato). When the compounds of the present invention are applied to paddy fields, they show also a strong herbicidal activity against main weeds by either or pre-emergence treatment or foliage treatment at the beginning of growth, and the dosages applied are not harmful to rice plants.

Further, the compounds of the present invention are very useful as herbicides not only for paddy rice but also for various crops, vegetables, orchards, turfs, pasture lands, tea gardens, mulberry farms, rubber farms, forest lands and non-cultivated lands.

Further, in properly applied dosage the compounds of the present invention are not harmful to mammals and fish, and they can practically be used without doing damage to useful agricultural crops.

The triazole compounds II-A, intermediates for producing the present compounds I-A, exhibit fungicidal activity against various pathogens which damage to agricultural crops. The intermediates II-A also exhibit a herbicidal and plant growth regulating action. It is also a fact, however, that the present compounds I-A have a far stronger activity against a wider range of plant pathogens and a far stronger herbicidal and plant growth regulating action than the compounds II-A.

More specific methods for producing the present compounds will be given below:

Method A: Reduction of the triazole compound II

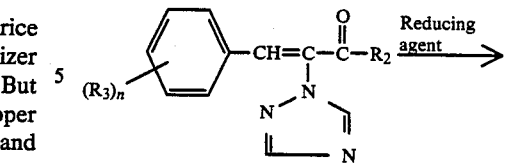

II-A isomer

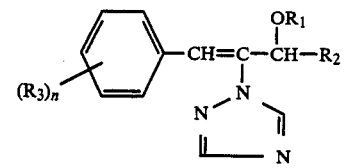

I'-A isomer (R₁ = H)

wherein $R_2$, $R_3$ and n are as defined above.

The I'-A isomer is produced by reducing the II-A isomer in a suitable solvent with a metal hydride complex (e.g. lithium aluminum hydride, sodium borohydride) or aluminum alkoxide (e.g. aluminum isopropoxide). The II-A isomer to be reduced can be obtained in a pure form, for example, by applying fractional crystallization or column chromatography to the mixture of the geometrical isomers of a triazole compound (II) produced according to the following reaction equation. The II-A isomer can also be obtained in a good yield, for example, by irradiating the mixture with ultraviolet rays to carry out photoisomerization. More detailed explanation will be given hereinafter with reference to Methods C and D.

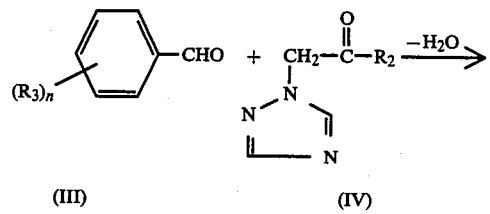

(III)     (IV)

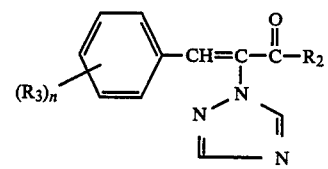

(II)

wherein $R_2$, $R_3$ and n are as defined above.

The solvent used in the reduction with a metal hydride complex includes for example ether (e.g. diethyl ether, tetrahydrofuran) and alcohols (e.g. methanol, ethanol, isopropanol). When sodium borohydride is used as the metal hydride complex, the reaction is achieved by mixing 1 mole of the II-A isomer and 0.25 to 2 moles of sodium borohydride in a solvent. The reaction temperature is preferably within a range of 0° C. to room temperature. The solvent used includes for example ether (e.g. diethyl ether, tetrahydrofuran) and alcohols (e.g. methanol, ethanol, isopropanol). When lithium aluminum hydride is used as the metal hydride complex, the reaction is achieved by dissolving lithium aluminum hydride of 0.25 to 0.8 time by mole based on the II-A isomer is a solvent and adding the resulting solution to a solution of the isomer in the same solvent. The reaction temperature is preferably within a range of $-60°$ C. to 70° C. The solvent used includes ethers (e.g. diethyl ether, tetrahydrofuran). After completion of the reaction, water or an aqueous dilute acid is added to the reaction solution, and after neutralization with an alkali if necessary, the deposited crystals are collected by filtration or extracted with an organic solvent sparingly soluble in water. The subsequent treatment is carried out by the common methods.

When aluminum isopropoxide is used as reducing agent, it is preferred to use such solvents as alcohols (e.g. isopropanol) or aromatic hydrocarbons (e.g. benzene). It is a common practice to allow 1 mole of the II-A isomer to react with 1 to 2 moles of aluminum isopropoxide at a temperature between room temperature and 100° C. The resulting aluminum compound is decomposed with a dilute sulfuric acid or an aqueous sodium hydroxide solution, followed by extraction with an organic solvent sparingly soluble in water. The subsequent treatment is carried out by the common methods.

The salts of the I'-A isomer refer to those obtained with plant-physiologically acceptable acids such as hydrohalogenic acid (e.g. hydrobromic acid, hydrochloric acid, hydroiodic acid), carboxylic acids (e.g. acetic acid, trichloroacetic acid, maleic acid, succinic acid), sulfonic acids (e.g. p-toluenesulfonic acid, methanesulfonic acid), nitric acid, sulfuric acid and phosphoric acid. If necessary, these salts are produced by the conventional methods.

Method B: Etherification of I'-A isomer

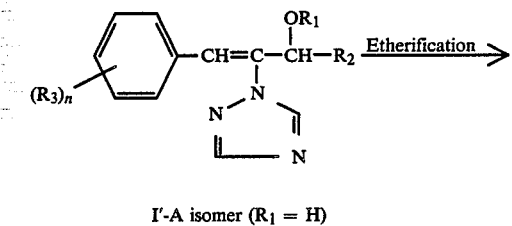

I'-A isomer ($R_1 = H$)

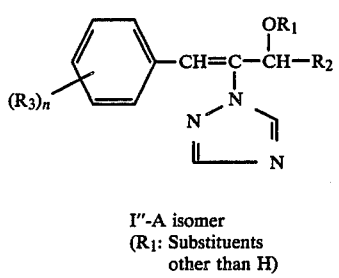

I"-A isomer
($R_1$: Substituents other than H)

wherein $R_1$, $R_2$, $R_3$ and n are as defined above.

The present compounds, I"-A isomer, are obtained by reacting I'-A isomer with a reactive $C_1$–$C_4$ alkyl, $C_3$–$C_4$ alkenyl or 2-propynyl derivative in a suitable solvent in the presence of a base. The reactive derivative includes for example alkyl-, alkenyl- or alkynyl-halides (e.g. methyl iodide, allyl bromide, propargyl bromide), sulfate compounds (e.g. dimethyl sulfate, diethyl sulfate) and sulfonate compounds (e.g. p-toluenesulfonate, naphthalenesulfonate). The solvent includes for example general inert organic solvents such as diethyl ether, tetrahydrofuran, dioxane, benzene, toluene, xylene and dimethylformamide. This reaction may be carried out in the presence of water using a phase transfer catalyst known as a reaction accelerator (e.g. triethylbenzylammonium chloride, trimethylbenzylammonium bromide). The base includes for example suitable strong bases (e.g. alkali metal hydrides such as sodium hydride, alkali metal amides such as sodium amide), carbonates (e.g. sodium carbonate, potassium carbonate) and alkali metal hydroxides (e.g. potassium hydroxide, sodium hydroxide).

This reaction is achieved by mixing I'-A isomer, a reactive $C_1$–$C_4$ alkyl, $C_3$–$C_4$ alkenyl or 2-propynyl derivative and a base, preferably in an equimolar ratio in a suitable solvent. The reaction is carried out within a range of 0° to 100° C., preferably 20° to 60° C. Sometimes, it is favorable to firstly react I'-A isomer with a suitable strong base (e.g. alkali metal hydrides, alkali metal amides) in an inert solvent and then to react the resulting alkali metal salt with a reactive $C_1$–$C_4$ alkyl, $C_3$–$C_4$ alkenyl or 2-propynyl derivative.

In some cases, the following way is desirable to isolate the present compounds I"-A: The reaction mixture is freed from the solvent by evaporation, water and an organic solvent sparingly soluble in water are added to the residue, the organic layer after extraction is separated and then purification is carried out by the usual methods.

The salts of the I"-A isomer refer to those obtained with physiologically acceptable acids such as hydrohalogenic acid (e.g. hydrobromic acid, hydrochloric acid, hydroiodic acid), carboxylic acids (e.g. acetic acid, trichloroacetic acid, maleic acid, succinic acid), sulfonic acids (e.g. p-toluenesulfonic acid, methanesulfonic acid), nitric acid, sulfuric acid and phosphoric acid. If necessary, these salts are produced by the conventional methods.

The present invention will be illustrated in more detail with reference to the following examples. Unless otherwise stated, NMR spectrum in the examples is indicated by δ values with deutero chloroform as a solvent and tetramethylsilane as an internal standard.

EXAMPLE 1

Synthesis of the I'-A isomer of 1-(4-chlorophenyl)-4,4-dimethyl-2-(1,2,4-triazole-1-yl)-1-pentene-3-ol (Compound No. 1) by Method A The II-A isomer (2.9 g, 0.01 mole; m.p. 108°–109° C.) of 1-(4-chlorophenyl)-4,4-dimethyl-2-(1,2,4-triazole-1-yl)-1-pentene-3-one (Compound No. 1') was dissolved in methanol (50 ml). Sodium borohydride (0.38 g, 0.01 mole) was added thereto while keeping the temperature of the reaction solution at 20° C. or less with ice-cooling. The reaction mixture was kept at 20° C. for 3 hours, and then decomposed with addition of water (100 ml) and acetic acid (1 ml). The organic layer was extracted with ethyl acetate (100 ml), and the extract was washed with a 5% aqueous sodium hydrogen carbonate solution (50 ml) and dried over anhydrous sodium sulfate. The solvent was then removed under reduced pressure, and the residue obtained was recrystallized from isopropanol to obtain 2.0 g (yield 69%) of the I'-A isomer having a melting point of 153°–155° C. The elementary analysis and NMR spectrum of the compound are shown below.

| Elementary analysis: | C (%) | H (%) | N (%) | Cl (%) |
|---|---|---|---|---|
| Calculated (as $C_{15}H_{18}N_3OCl$) | 61.74 | 6.23 | 14.40 | 12.15 |
| Found | 61.82 | 6.33 | 14.38 | 12.15 |

NMR spectrum: 8.52 (1H, s, triazole proton), 7.98 (1H, s, triazole proton), 7.30 (4H, s, phenyl proton), 6.91 (1H, s, olefin proton), 4.56 (2H, broad singlet, hydroxyl proton and methine proton carrying an OH group), 0.66 (9H, s, butyl proton).

COMPARATIVE EXAMPLE 1

Synthesis of the I'-B isomer of 1-(4-chlorophenyl)-4,4-dimethyl-2-(1,2,4-triazole-1-yl)-1-pentene-3-ol (Compound No. 1)

The II-B isomer (2.9 g, 0.01 mole; m.p. 78°–79° C.) of 1-(4-chlorophenyl)-4,4-dimethyl-2-(1,2,4-triazole-1-yl)-1-pentene-3-one (Compound No. 1') was dissolved in methanol (50 ml). The isomer was allowed to react with sodium borohydride and then treated in the same manner as in Example 1. The residue obtained was recrystallized from a 1:10 mixture of carbon tetrachloride and n-hexane to obtain 2.2 g (yield 76%) of the I'-B isomer (m.p. 116°–117° C.) of Compound No. 1. The elementary analysis and NMR spectrum of the compound are shown below.

| Elementary analysis: | C (%) | H (%) | N (%) | Cl (%) |
|---|---|---|---|---|
| Calculated (as $C_{15}H_{18}N_3OCl$) | 61.74 | 6.23 | 14.40 | 12.15 |
| Found | 61.80 | 6.25 | 14.52 | 12.09 |

NMR spectrum: 7.92 (s, triazole proton), 7.77 (1H, s, triazole proton), 7.05 (2H, d, phenyl proton, J=9 Hz), 6.58 (2H, d, phenyl proton, J=9 Hz), 6.66 (1H, s, olefin proton), 4.28 (1H, d, methine proton carrying an OH group, J=6 Hz) 3.21 (1H, d, hydroxyl proton, J=6 Hz), 0.80 (9H, s, butyl proton).

EXAMPLE 2

Synthesis of the I'-A isomer of 3-(4-chlorophenyl)-1-(1-methylcyclopropyl)-2-(1,2,4-triazole-1-yl)-2-propene-1-ol (Compound No. 30) by Method A The II-A isomer (2.9 g, 0.01 mole; m.p. 89°–92° C.) of 3-(4-chlorophenyl)-1-(1-methylcyclopropyl)-2-(1,2,4-triazole-1-yl)-2-propene-1-one (Compound No. 29') characterized by the NMR spectrum described below was dissolved in methanol (50 ml). Sodium borohydride (0.38 g, 0.01 mole) was added thereto while keeping the reaction temperature at 20° C. or less with ice-cooling. The reaction solution was kept at 20° C. for 3 hours, and then decomposed with addition of water (100 ml) and acetic acid (2 ml). The organic layer was extracted with chloroform (100 ml), and the extract was washed with a 5% aqueous sodium hydrogen carbonate solution (50 ml) and dried over anhydrous magnesium sulfate. The solvent was then removed under reduced pressure, and the residue obtained was crystallized from a carbon tetrachloride/n-hexane (1:1) mixture (5 ml) to obtain 2.4 g (yield 85%) of the entitled compound.

The NMR spectrum of the starting material, II-A isomer of 3-(4-chlorophenyl)-1-(1-methylcyclopropyl)-2-(1,2,4-triazole-1-yl)-2-propene-1-one, is as follows: 8.28 (1H, s, triazole proton), 8.07 (1H, s, triazole proton), 7.32 (4H, s, phenyl proton), 7.19 (1H, s, olefin proton), 1.45–1.15 (2H, m, methylene proton of cyclopropyl group), 1.25 (3H, s, methyl proton), 0.99–0.75 (2H, m, methylene proton of cyclopropyl group).

COMPARATIVE EXAMPLE 2

Synthesis of the I'-B isomer of 3-(4-chlorophenyl)-1-(1-methylcyclopropyl)-2-(1,2,4-triazole-1-yl)-2-propene-1-ol (Compound No. 30)

The II-B isomer (2 g, 0.007 mole; m.p. 74°–75° C.) of 3-(4-chlorophenyl)-1-(1-methylcyclopropyl)-2-(1,2,4-triazole-1-yl)-2-propene-1-one (Compound No. 29') characterized by the NMR spectrum described below was reduced, in the same manner as in Example 2, with sodium borohydride (0.27 g, 0.007 mole) in methanol (50 ml). Thus, 1.7 g (yield 85%) of the entitled compound was obtained.

The NMR spectrum of the starting material, II-B isomer of 3-(4-chlorophenyl)-1-(1-methylcyclopropyl)-2-(1,2,4-triazole-1-yl)-2-propene-1-one, is as follows: 8.12 (1H, s, triazole proton), 8.03 (1H, s, triazole proton), 7.55 (1H, s, olefin proton), 7.21 (2H, d, phenyl proton, J=8 Hz), 6.81 (2H, d, phenyl proton, J=8 Hz), 1.50–1.25 (2H, m, methylene proton of cyclopropyl group), 1.28 (3H, s, methyl proton), 0.90–0.65 (2H, m, methylene proton of cyclopropyl group).

EXAMPLE 3

Synthesis of I"-A isomer of 1-(4-chlorophenyl)-4,4-dimethyl-3-methoxy-2-(1,2,4-triazole-1-yl)-1-pentene (Compound No. 35) by Method B The I'-A isomer (2 g) of 1-p-chlorophenyl-4,4-dimethyl-2-(1,2,4-triazole-1-yl)-1-pentene-3-ol (Compound No. 1) was dissolved in dimethylformamide (20 cc), and 65% oily sodium hydride (0.26 g) was added thereto. After stirring for 1 hour at room temperature, the reaction mixture was cooled to 10° C., and methyl iodide (1 g) was added. After standing at room temperature for 20 hours, the solvent was removed under reduced pressure, and the residue obtained was extracted with addition of ice water (100 g) and chloroform (100 cc). The organic layer was dried over anhydrous magnesium sulfate, and the solvent was removed under reduced pressure. The oily crude product obtained was purified by column chromatography on silica gel (acetone:n-hexane=1:10) and further recrystallized from a carbon tetrachloride/n-hexane (1:2) mixture to obtain 1.6 g of the entitled compound (m.p. 63°–66° C.).

COMPARATIVE EXAMPLE 3

Synthesis of the I"-B isomer of 1-p-chlorophenyl-4,4-dimethyl-3-methoxy-2-(1,2,4-triazole-1-yl)-1-pentene (Compound No. 35)

The I'-B isomer (2 g) of 1-(4-chlorophenyl)-4,4-dimethyl-2-(1,2,4-triazole-1-yl)-pentene-3-ol (Compound No. 1) was dissolved in dimethylformamide (20 cc), and 65% sodium hydride (0.26 g) was added thereto. After stirring at room temperature for 1 hour, the reaction mixture was cooled to 10° C., and methyl iodide (1 g) was added. The reaction mixture was kept at 10° C. for 1 hour and then allowed to stand at room temperature for 16 hours. Dimethylformamide was removed under reduced pressure, and the residue was extracted with addition of ice water (100 g) and chloroform (100 cc). The organic layer was dried over anhydrous magnesium sulfate, and the solvent was removed under reduced pressure. The resulting crude product was purified by column chromatography on silica gel (acetone:n-hexane=1:10) to obtain 1.0 g of the entitled compound as an oily product.

Refractive index $n_D^{27}$ 1.5435.

| Elementary analysis: | C (%) | H (%) | N (%) | Cl (%) |
|---|---|---|---|---|
| Found | 62.90 | 6.60 | 13.77 | 11.50 |
| Calculated | 62.84 | 6.59 | 13.74 | 11.59 |

| -continued | | | | |
|---|---|---|---|---|
| Elementary analysis: | C (%) | H (%) | N (%) | Cl (%) |
| (as $C_{16}H_{20}N_3ClO$) | | | | |

The present compounds (I-A isomer) obtained by Methods A and B are shown in Table 1. For comparison, the data on I-B isomer was shown together. Unless otherwise stated, NMR spectrum in the table is indicated in δ values with CDCl$_3$ as a solvent and tetramethylsilane as an internal standard. The I'-A isomer and I"-A isomer are generically called I-A isomer, and the I'-B isomer and I"-B isomer are also generically called I-B isomer. This generic indication is also used in the test examples described below.

TABLE 1

[I]

Structure: (R$_3$)$_n$-phenyl-CH=C(OR$_1$)-CH(R$_2$)-N(triazole)

| Compound No. | R$_1$ | R$_2$ | (R$_3$)$_n$ | Kind of geometrical isomer | Physical constant | Triazole proton | Olefin proton | NMR spectrum OR$_1$–CH–R$_2$ | R$_2$ proton |
|---|---|---|---|---|---|---|---|---|---|
| 1 | H | C(CH$_3$)$_3$ | 4-Cl | I-A | mp 153–155° C. | 8.52, 7.98 | 6.91 | 4.56 | 0.66 |
|  | " | " |  | I-B | mp 116–117° C. | 7.92, 7.77 | 6.60 | 4.28 (d, J = 6 Hz) | 0.80 |
| 2 | " | " | 2,4-di-Cl | I-A | mp 148–149° C. | 8.45, 7.97 | 6.80 | 4.35 | 0.63 |
|  | " | " |  | I-B | mp 146–147° C. | 7.90, 7.65 | 6.72 | 4.36 (d, J = 6 Hz) | 0.88 |
| 3 | " | " | 4-Br | I-A | mp 146–149° C. | 8.55, 8.02 | 6.90 | 4.58 (d, J = 9 Hz) | 0.70 |
|  | " | " |  | I-B | mp 127–128° C. | 7.98, 7.82 | 6.62 | 4.30 (d, J = 5 Hz) | 0.80 |
| 4 | " | " | 4-F | I-A | mp 203–204° C. | 8.82, 8.09 | 7.04 | 4.61 (d, J = 4 Hz) | 0.63 |
|  | " | " |  | I-B | mp 82–85° C. | 7.93, 7.76 | 7.14 | 4.25 | 0.81 |
| 5 | " | " | 2-Cl | I-A | mp 168–170° C. | 8.90, 8.11 | 7.08 | 4.50 (d, J = 4 Hz) | 0.59*5 |
|  | " | " |  | I-B | mp 109–110° C. | 8.02, 7.75 | 6.89 | 4.95 | 0.82 |
| 6 | " | " | 4-phenyl | I-A | mp 158–161° C. | 8.50, 8.01 | 6.97 | 4.73 (d, J = 4 Hz) | 0.70 |
|  | " | " |  | I-B | mp 172–173° C. | 7.98, 7.84 | 6.68 | 4.30 | 0.82 |
| 7 | " | " | 4-OCH$_3$ | I-A | mp 162–163° C. | 8.36, 7.95 | 6.82 | 4.63 (d, J = 9 Hz) | 0.68 |
|  | " | " |  | I-B | mp 102–104° C. | 8.10, 7.95 | 6.72 | 4.25 | 0.84 |
| 8 | " | " | 4-CN | I-A | mp 191–194° C. | 8.56, 8.00 | 6.98 | 4.54 (d, J = 8 Hz) | 0.68 |
|  | " | " |  | I-B | mp 111–114° C. | 8.09, 7.94 | 6.79 | 4.40 | 0.85 |
| 9 | " | " | H | I-A | mp 153–155° C. | 8.45, 7.95 | 6.92 | 4.63 | 0.66 |
|  | " | " |  | I-B | mp 88–90° C. | 7.91, 7.62 | 6.65 | 4.28 | 0.83 |
| 10 | " | " | 4-CH$_3$ | I-A | mp 155–157° C. | 8.50, 7.99 | 6.92 | 4.80–4.30 (m) | 0.68 |
|  | " | " |  | I-B | mp 127–128° C. | 8.05, 7.85 | 6.70 | 4.30 | 0.82 |
| 11 | " | " | 4-NO$_2$ | I-A | mp 194–195° C. | 8.90, 8.23 | 7.15 | 4.69 (d, J = 5 Hz) | 0.66*5 |
|  | " | " |  | I-B | mp 123–124° C. | 8.09, 7.99 | 6.85 | 4.46 (d, J = 5 Hz) | 0.85 |
| 12 | " | " | 4-phenoxy | I-A | mp 164–165° C. | 8.47, 7.98 | 7.43–6.80 (m)*1 | 4.80–4.25 (m) | 0.70 |
| 13 | " | CH$_3$ | 4-Cl | I-A | mp 88–89° C. | 8.52, 8.02 | 6.90 | 5.11 (m) | 1.35 (d, J = 6 Hz) |
|  | " | " |  | I-B | mp 141–142° C. | 8.07, 7.84 | 6.77 | 4.95–4.50 (m) | 1.31 (d, J = 6 Hz) |
| 14 | " | -CH(CH$_2$)(CH$_2$) cyclopropyl | " | I-A | mp 110–112° C. | 8.62, 8.02 | 6.96 | 4.14 (d, J = 7 Hz) | 1.10–0.65 (1H, m), 0.60–0.01 (4H, m) |
|  | " | " |  | I-B | n$_D^{26}$ 1.5600 | 8.08, 7.92 | 6.84 | 4.00–3.65 (m) | 1.15–0.65 (1H, m), 0.60–0.01 (4H, m) |
| 15 | " | -CH(CH$_3$)(CH$_3$) isopropyl | " | I-A | mp 127–128.5° C. | 8.59, 8.02 | 7.01 | 4.36 (d, J = 9 Hz) | 1.54 (1H, m), 1.01 (3H, d, J = 6 Hz), 0.72 (3H, d, J = 6 Hz) |
|  | " | " |  | I-B | mp 106–107° C. | 8.10, 7.89 | 6.75 | 4.23 (dd, J = 6 Hz, 7 Hz) | 1.52 (1H, m), 1.00 (3H, d, J = 6 Hz), 0.97 (3H, d, J = 6 Hz) |
| 16 | " | C(CH$_3$)$_3$ | 3-CF$_3$ | I-A | n$_D^{25}$ 1.5055 | 8.73, 8.06 | 7.10 | 5.00–4.50 (m) | 0.74 |
|  | " | " |  | I-B | mp 117–119° C. | 8.05, 7.88 | 6.78 | 4.36 | 0.85 |

TABLE 1-continued

[I]

$$(R_3)_n\text{-C}_6H_4\text{-CH=C}(R_2)\text{-CH}(OR_1)\text{-CH}_2\text{-N(triazole)}$$

| Compound No. | R₁ | R₂ | (R₃)ₙ | Kind of geometrical isomer | Physical constant | Triazole proton | Olefin proton | NMR spectrum OR₁ —CH—R₂ | R₂ proton |
|---|---|---|---|---|---|---|---|---|---|
| 17 | | | 2-Cl—5-NO₂ | I-A | mp 136-139° C. | 8.79, 8.45–7.90 (m)*² | 7.05 | 4.43 (d, J = 8 Hz) | 0.71 |
| 18 | " | " | 3-F—4-OCH₃ | I-A | mp 192-194° C. | 8.42, 7.96 | 6.87 | 4.43 (d, J = 5 Hz) | 0.88 |
| | | | | I-B | mp 167-168° C. | 8.52, 8.00 | 7.30–6.80 (m)*¹ | 4.80–4.40 (m) | 0.70 |
| 19 | " | " | 2-OCH₃ | I-A | mp 67-70° C. | 8.09, 7.98 | 6.90–6.35 (m)*¹ | 4.40–4.10 (m) | 0.81 |
| | | | | I-B | mp 176.5° C. | 8.55, 8.01 | 6.95 | 4.57 | 0.67 |
| 20 | " | —(CH₂)₃—CH₃ | 4-Cl | I-A | mp 187° C. | 7.93, 7.76 | 6.81 | 4.37 (d, J = 5 Hz) | 0.81 |
| | | | | I-B | mp 70-73° C. | 8.55, 8.01 | 6.95 | 5.10–4.70 (m) | 1.70–0.60 (m) |
| 21 | " | C(CH₃)₃ | 2,3-di-Cl | I-A | mp 164-166° C. | 8.06, 7.86 | 6.76 | 4.90–4.30 (m) | 1.70–0.70 (m) |
| | | | | I-B | mp 84-85° C. | 8.72, 8.05 | 7.00 | 4.41 (d, J = 8 Hz) | 0.67 |
| 22 | " | —(CH₂)₅CH₃ | 4-Cl | I-A | nD²⁶ 1.5413 | 7.99, 7.73 | 6.86 | 4.45 (d, J = 6 Hz) | 0.85 |
| | | | | I-B | mp 70-72° C. | 8.56, 7.99 | 6.96 | 5.10–4.60 (m) | 1.80–0.70 (m) |
| 23 | " | C(CH₃)₃ | 4-CH(CH₃)₂ | I-A | nD²⁴ 1.5288 | 8.03, 7.84 | 6.74 | 4.70–4.20 (m) | 1.70–0.70 (m) |
| | | | | I-B | nD²⁴ 1.5392 | 8.49, 7.95 | 6.91 | 4.90–4.40 (m) | 0.70 |
| 24 | " | " | 4-OCH₂CH₃ | I-A | mp 142-144° C. | 8.04, 7.94 | 6.71 | 4.32 | 0.82 |
| | | | | I-B | mp 131-132° C. | 8.40, 7.96 | 6.81 | 4.61 | 0.68 |
| 25 | " | —CH(CH₃)CH(CH₃)CH₃ (isobutyl-like) | 4-Cl | I-A | mp 126-128° C. | 8.14, 7.99 | 6.75 | 4.30 (d, J = 6 Hz) | 0.82 |
| | | | | | | 8.50, 8.02 | 6.89 | 5.20–4.70 (m) | 1.90–1.25 (3H, m), 0.82 (6H, dd, J = 6 Hz, 2 Hz) |
| | | | | I-B | mp 109-110° C. | 8.08, 7.85 | 6.75 | 4.82–4.46 (m) | 1.90–1.20 (3H, m), 0.93 (6H, dd, J = 6 Hz, 2 Hz) |
| 26 | " | —CH(CH₃)CH₂CH₃ | 4-Cl | I-A | mp 74-75.5° C. | 8.57, 8.00 | 6.98 | 4.70–4.00 (m) | 1.40–0.60 (m) |
| | | | | I-B | nD²³ 1.5452 | 8.03, 7.81 | 6.80 | 4.50–4.10 (m) | 1.60–0.60 (m) |
| 27 | " | C(CH₃)₃ | " | I-A | mp 151-152° C. | *⁴ | | | |
| | | | | I-B | mp 168-169° C. | *⁴ | | | |
| 28 | " | CH₂CH₂CH₃ | " | I-A | nD²⁴ 1.5639 | 8.60, 7.88 | 6.95 | 5.10–4.70 (m) | 2.00–0.60 (m) |
| | | | | I-B | mp 114-115° C. | 8.06, 7.84 | 6.72 | 4.70–4.30 (m) | 1.70–0.70 (m) |
| 29 | " | —CH(CH₃)CH₂CH₃ | 2,4-di-Cl | I-A | mp 125-127° C. | 8.55, 8.02 | 6.93 | 4.25 (t, J = 9 Hz) | 1.80–0.50 (m) |
| | | | | I-B | mp 127-130° C. | 7.98, 7.70 | 6.80 | 4.70–4.20 (m) | 1.60–0.80 (m) |

TABLE 1-continued

[I]

(R₃)ₙ—C₆H₄—CH=C(OR₁)—CH(R₂)—N(N=CH-N=CH)

| Compound No. | R₁ | R₂ | (R₃)ₙ | Kind of geometrical isomer | Physical constant | Triazole proton | Olefin proton | NMR spectrum OR₁ —CH—R₂ | R₂ proton |
|---|---|---|---|---|---|---|---|---|---|
| 30 | " | CH₃<br>—C(—CH₂—CH₂—)CH₂ | 4-Cl | I-A | mp 103–105° C. | 8.50, 8.00 | 6.96 | 5.00–4.70 (m) | 0.88 (3H, S), 0.60–0.30 (2H, m)<br>0.25–0.00 (2H, m) |
| | | | | I-B | mp 120–122° C. | 8.08, 7.86 | 6.94 | 4.01 | 1.06 (3H, S), 0.50–0.00 (4H, m) |
| 31 | " | " | 2,4-di-Cl₂ | I-A | mp 118–119° C. | 8.46, 8.01 | 6.90 | 4.56–4.52 (m) | 0.82 (3H, S), 0.42 (3H, S), 0.05 (3H, S)<br>0.65–0.00 (4H, m) |
| | | | | I-B | mp 139–140° C. | 7.96, 7.70 | 7.02 | 4.11 (d, J = 4 Hz) | 1.11 (3H, S), 0.65–0.00 (4H, m) |
| 32 | " | " | 4-Br | I-A | mp 105–107° C. | 8.51, 8.01 | 6.95 | 4.95–4.75 (m) | 0.86 (3H, S), 0.55 (2H, m), 0.20–0.00 (2H, m) |
| | | | | I-B | mp 139–140° C. | 7.96, 7.70 | 7.02 | 4.11 (d, J = 4 Hz) | 1.11 (3H, S), 0.65–0.00 (4H, m) |
| 33 | " | " | 4-F | I-A | mp 120–124° C. | 8.54, 8.05 | 7.55–6.80 (m)*¹ | 4.86 (d, J = 8 Hz) | 0.90 (3H, S), 0.50–0.35 (2H, m),<br>0.20–0.00 (2H, m) |
| | | | | I-B | mp 81–83° C. | 8.04, 7.81 | 6.98–6.70 (m)*¹ | 4.10–3.95 (m) | 1.06 (3H, S), 0.40–0.00 (4H, m) |
| 34 | " | " | H | I-A | mp 125–127° C. | 8.49, 7.92 | 7.00 | 4.91 (d, J = 7 Hz) | 0.85 (3H, S), 0.60–0.30 (2H, m),<br>0.25–0.00 (2H, m) |
| | | | | I-B | mp 120–121° C. | 8.09, 7.83 | 7.30–6.65 (m)*¹ | 4.04 (d, J = 4 Hz) | 1.06 (3H, S), 0.35–0.00 (4H, m) |
| 35 | CH₃ | C(CH₃)₃ | 4-Cl | I-A | mp 63–66° C. | 8.56, 8.00 | 7.35 | 4.10 | 0.73 |
| 36 | CH₂CH₃ | " | " | I-B | n_D²⁷ 1.5435 | — | — | — | — |
| | | | | I-A | n_D²⁷ 1.5452 | 8.58, 7.95 | 7.29 | 4.16 | 0.74 |
| 37 | —(CH₂)₃CH₃ | " | " | I-B | n_D²⁷ 1.5380 | — | — | — | — |
| 38 | CH₂CH=CH₂ | " | " | I-A | n_D²⁶ 1.5390 | 8.60, 7.95 | 7.27 | 4.13 | 0.74 |
| | | | | I-A | n_D²⁶ 1.5464 | 8.52, 7.93 | 7.27 | 4.23 | 0.77 |
| 39 | CH₂CH=CHCH₃ | " | " | I-B | n_D²⁷ 1.5310 | — | — | — | — |
| | | | | I-A | n_D²⁶ 1.5503 | 8.57, 7.94 | 7.25 | 4.22 | 0.75 |
| 40 | CH₃ | " | 4-F | I-A | *³ | — | — | — | — |
| 41 | CH₂CH₂CH₃ | " | " | I-A | mp 72–73° C. | 8.57, 8.00 | 7.23 | 4.09 | 0.74 |
| 42 | CH₂CH=CH₂ | " | " | I-A | n_D²⁵ 1.5195 | 8.68, 8.03 | 7.24 | 4.17 | 0.75 |
| 43 | CH₃ | " | H | I-A | n_D²⁵ 1.5220 | 8.55, 7.96 | 7.19 | 4.24 | 0.77 |
| | | | | I-A | n_D²⁶ 1.5382 | 8.51, 7.98 | 7.36 | 4.12 | 0.74 |
| 44 | CH₃ | " | 4-Br | I-B | n_D²⁵ 1.5355 | — | — | — | — |
| 45 | CH₂CH=CH₂ | " | " | I-A | n_D²⁶ 1.5619 | 8.50, 7.93 | 7.27 | 4.00 | 0.72 |
| | | | " | I-A | n_D²⁶ 1.5638 | 8.54, 7.94 | 7.23 | 4.25 | 0.79 |
| 46 | CH₃ | " | 4-NO₂ | I-A | n_D²³ 1.5550 | 7.96, 7.32 | 6.69 | 3.85 | 0.85 |
| 47 | CH₂C≡CH | " | 4-Cl | I-B | n_D²⁶ 1.5450 | 8.52, 7.94 | 7.31 | 4.44 | 0.75 |

TABLE 1-continued

[I]

(structure: phenyl ring with (R3)n substituents, CH=C(OR1)-CH(R2)- connected to triazole ring)

| Compound No. | R₁ | R₂ | (R₃)ₙ | Kind of geometrical isomer | Physical constant | Triazole proton | Olefin proton | NMR spectrum OR₁ \| —CH—R₂ | R₂ proton |
|---|---|---|---|---|---|---|---|---|---|
| 48 | CH₃ | " | 4-CH(CH₃)(CH₃) | I-A | $n_D^{24}$ 1.5360 | 8.52, 8.00 | 7.35 | 4.20 | 0.75 |
| 49 | CH₂CH=CH₂ | " | 2,3-di-Cl | I-A | $n_D^{22}$ 1.5570 | 8.61, 7.99 | 7.30 | 4.10 | 0.75 |
| 50 | CH₂CH=CH₂ | " | 2-OCH₃ | I-A | $n_D^{22}$ 1.5380 | 8.52, 7.96 | 7.35–7.15 (m)*¹ | 4.20 | 0.75 |
| 51 | CH₃ | " | 2,4-di-Cl | I-A | $n_D^{25}$ 1.5535 | 8.68, 8.07 | 7.40 | 3.97 | 0.76 |
|  |  |  | " | I-B | $n_D^{27}$ 1.5461 |  |  |  |  |
| 52 | CH₂CH=CH₂ | " | 3,5-di-Cl | I-A | $n_D^{25}$ 1.5510 | 8.62, 8.00 | 7.30 | 4.08 | 0.75 |
| 53 |  |  |  | I-A | mp 161–162° C. | 8.60, 8.00 | 6.88 | 4.54 | 0.73 |
|  |  |  |  | I-B | mp 120–121° C. | 8.02, 7.84 | 6.72–6.55 (m)*¹ | 4.30 (d, J = 6 Hz) | 0.81 |
| 54 | H | " | 4-C₂H₅ | I-A | mp 85–86° C. | 8.52, 8.00 | 6.92 | 4.71 (d, J = 7 Hz) | 0.70 |
|  |  |  |  | I-B | mp 136–137° C. | 8.03, 7.84 | 6.69 | 4.26 (d, J = 6 Hz) | 0.81 |
| 55 | H | " | 2-F—4-Cl | I-A | mp 159–160° C. | 8.61, 8.02 | 7.52–6.80 (m)*¹ | 4.51 | 0.71 |
|  |  |  |  | I-B | mp 128–129° C. | 8.04, 7.95 | 6.75 | 4.42 (d, J = 6 Hz) | 0.82 |
| 56 | H | " | 3,4,5-tri-OCH₃ | I-A | mp 155–156° C. | 8.61, 8.00 | 6.94 | 5.00–4.60 (m) | 0.74 |
|  |  |  |  | I-B | mp 113–114° C. | 8.07, 8.02 | 6.60 | 4.40–4.10 (m) | 0.81 |

Note:
*¹Olefin proton and phenyl proton appear at the same position.
*²Triazole proton and phenyl proton appear at the same position.
*³Resinous product
*⁴Hydrochloric acid salt
*⁵Solvent: (CD₃)₂SO Next, explanation will be given to the production of the II-A isomer of the triazole compound (II), which is a starting material for the I'-A isomer of the triazole compound (I).

Method C: Isomerization of the II-B isomer or a mixture of the II-B and II-A isomers of the traizole compound (II)

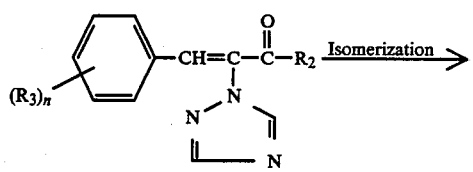

II-B isomer or a mixture of II-B and II-A isomers

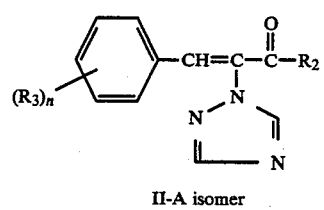

II-A isomer wherein $R_2$, $R_3$ and n are as defined above.

The II-A isomer can be produced by irradiating the II-B isomer or a mixture of the II-B and II-A isomers with rays from UV lamps or xenon lamps, or experimentally with rays from fluorescent lamps or the sun, in a solvent inert to the rays. As the solvent commonly used, there may be given for example alcohols (e.g. methanol, ethanol, propanol), ethers (e.g. tetrahydrofuran, dioxane), ketones (e.g. acetone, methyl ethyl ketone, methyl isobutyl ketone), aliphatic hydrocarbons (e.g. hexane, cyclohexane, petroleum ether), and aromatic hydrocarbons (e.g. benzene, toluene, xylene). The reaction may be carried out at temperatures at which the common photoisomerization is carried out, but actually temperatures between 0° C. and 100° C. are preferred. The reaction can of course be carried out with addition of a sensitizer used in the common photoreactions, for example phenylketones such as acetophenone and propiophenone, but great advantages can not particularly be found.

Next, a method for producing the triazole compound represented by the formula (II) will be illustrated Method D: Production of a mixture of the geometrical isomers of the triazole compound (II) and each isomer (II-B, II-A)

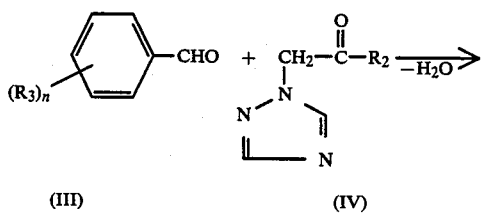

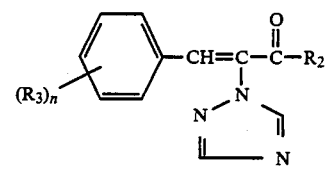

wherein $R_2$, $R_3$ and n are as defined above.

The triazole compound (II) is obtained by reacting 1 mole of a ketone of the formula (IV) with 1 to 2 moles of a benzaldehyde of the formula (III) in a suitable solvent in the presence of a basic catalyst. The basic catalyst includes for example alkali metal or alkaline earth metal hydroxides (e.g. sodium hydroxide, potassium hydroxide, calcium hydroxide), alkali metal alcoholates (e.g. sodium methylate, sodium ethylate, potassium methylate), carbonates (e.g. sodium carbonate, potassium carbonate), acetates (e.g. sodium acetate, potassium acetate), secondary amines (e.g. diethylamine, dipropylamine, pyrrolidine, piperidine, morpholine) and tertiary amines (e.g. triethylamine, tributylamine, pyridine, picoline, dimethylaniline), and it is used in amounts between 0.01 mole and 10.0 moles. The solvent includes for example alcohols (e.g. methanol, ethanol), aromatic hydrocarbons (e.g. benzene, toluene, xylene), ethers (e.g. diethyl ether, tetrahydrofuran, dioxane), water and mixtures thereof. The reaction is carried out within a range of 0° C. to the boiling point of the solvent.

When the basic catalyst is an acetate (e.g. sodium acetate, potassium acetate), a carbonate (e.g. sodium carbonate, potassium carbonate) or a tertiary amine, glacial acetic acid or acetic anhydride can also be used as a reaction solvent.

The triazole compound (II) thus obtained is a mixture of two geometrical isomers, i.e. II-A isomer and II-B isomer, in general, and each isomer can be isolated by column chromatography or fractional crystallization. The mixture of the geometrical isomers generally contains a larger proportion of II-B isomer than that of II-A isomer. All the II-A isomers of the ketone compound are of course novel compounds, and of the II-B isomers, those in which $R_2$ is a 1-methylcyclopropyl group are also novel compounds.

Next, Methods C and D will be illustrated in more detail with reference to the following examples.

EXAMPLE 4

Synthesis of 1-(4-chlorophenyl)-4,4-dimethyl-2-(1,2,4-triazole-1-yl)-1-pentene-3-one (Compound No. 1') by Method D α-(1,2,4-Triazole-1-yl)pinacolone (50 g), anhydrous potassium carbonate (41 g), acetic anhydride (200 ml) and 4-chlorobenzaldehyde (46.3 g) were mixed, and the mixture was heated to 90° C. for 12 hours with stirring. After cooling the reaction solution, the precipitates were removed by filtration. The filtrate was added dropwise to warm water (500 ml) of 60° C. to decompose acetic anhydride, and potassium carbonate was then added little by little to make the solution alkaline. The produced oily product was extracted with ethyl acetate (500 ml), and the organic layer was dried over anhydrous sodium sulfate and concentrated under reduced pressure. One drop of the residue was dissolved in acetone, and the acetone solution was gas-chromatographed under the conditions described below. Then, a peak corresponding to the II-A isomer was found at a retention time of 300 sec, and that corresponding to the II-B isomer at a retention time of 360 sec. The ratio of the both isomers was 19.8/61.2, i.e. about ⅓, as calculated from the percentage of each area.

The conditions of gas chromatography was as follows:

Apparatus: Nippon Denshi 20K gas chromatograph equipped with a FID detector
Column: Glass column of 1 m in length
  liquid phase: 5% XE-60
  carrier: Chromosorb W
Temperature (column): 200° C.
Temperature (injection): 240° C.
Carrier gas: nitrogen gas, 1 kg/cm$^2$ The residue was dissolved in benzene (100 ml). The solution was passed through a column packed with 100- to 200-mesh silica gel (1.2 kg) and column chromatographed with n-hexane/acetone (10:1) as a developing solvent. The fraction corresponding to each isomer was recrystallized from carbon tetrachloride to obtain 36 g (yield 41.6%) of a pure II-B isomer (m.p. 78°-79° C.) and 10 g (yield 11.5%) of a pure II-A isomer (m.p. 108°-109° C.). The developing solvent, n-hexane/acetone (10/3), was further passed through the column to recover 8 g of α-(1,2,4-triazole-1-yl)pinacolone. The elementary analysis and NMR spectrum of each isomer are shown below. The NMR spectrum was measured with deutero chloroform as solvent, and the chemical shift was expressed by δ values with tetramethylsilane as internal standard.

II-A isomer of 1-(4-chlorophenyl)-4,4-dimethyl-2-(1,2,4-triazole-1-yl)-1-pentene-3-one (Compound No. 1'):

| Elementary analysis: | C (%) | H (%) | N (%) | Cl (%) |
|---|---|---|---|---|
| Calculated (as C$_{15}$H$_{16}$N$_3$OCl) | 62.17 | 5.58 | 14.50 | 12.23 |
| Found | 62.32 | 5.60 | 14.41 | 12.20 |

NMR spectrum: 8.11 (1H, s, triazole proton), 7.90 (1H, s, triazole proton), 7.15 (4H, s, phenyl proton), 6.99 (1H, s, olefin proton), 0.99 (9H, s, butyl proton).

II-B isomer of 1-(4-chlorophenyl)-4,4-dimethyl-2-(1,2,4-triazole-1-yl)-1-pentene-3-one (Compound No. 1'):

| Elementary analysis: | C (%) | H (%) | N (%) | Cl (%) |
|---|---|---|---|---|
| Found | 62.35 | 5.59 | 14.38 | 12.18 |

NMR spectrum: 8.14 (1H, s, triazole proton), 7.98 (1H, s, triazole proton), 7.22 (2H, d, phenyl proton, J=8 Hz), 6.73 (2H, d, phenyl proton, J=8 Hz), 7.49 (1H, s, olefin proton), 1.22 (9H, s, butyl proton).

EXAMPLE 5

Synthesis of the II-A isomer of 1-(4-chlorophenyl)-4,4-dimethyl-2-(1,2,4-triazole-1-yl)-1-pentene-3-one by Method C The II-B isomer (8.0 g) of 1-(4-chlorophenyl)-4,4-dimethyl-2-(1,2,4-triazole-1-yl)-1-pentene-3-one obtained in Example 4 was dissolved in acetone (500 ml) and isomerized at 45° C. by means of a ultraviolet ray generator equipped with a 500-W high-pressure mercury lamp. In the course of the reaction, a trace amount of the reaction solution was sometimes sampled and measured for a ratio of the isomers [II-B isomer/II-A isomer] by gas chromatography under the same conditions as in Example 4. The results were as follows:

| Time (minute) | Ratio of isomers [II-B/II-A] |
|---|---|
| 0 | 100/0 |
| 20 | 10/90 |
| 60 | 6/94 |
| 120 | 6/94 |

After 2.5 hours, the reaction solution was transferred to a 500-ml eggplant-form flask, and acetone was removed under reduced pressure to obtain 7.9 g of crystals. The crystals were recrystallized from carbon tetrachloride to obtain 6.2 g (yield 78%) of crystals (m.p. 108°-109° C.). This compound was dissolved in acetone and gas-chromatographed in the conditions described above, but no peak corresponding to the II-B isomer was observed.

EXAMPLE 6

Synthesis of the II-A isomer from a mixture of the geometrical isomers of 1-(4-chlorophenyl)-4,4-dimethyl-2-(1,2,4-triazole-1-yl)-1-pentene-3-one (Compound No. 1')

The reaction mixture (10 g) containing the II-A and II-B isomers in a ratio of 1 to 3 obtained in Example 4 was irradiated with ultraviolet rays in the same conditions as in Example 5. After 1.5 hours, the ratio of II-A isomer to II-B isomer was measured by gas chromatography, and it was found that the ratio was about 19 to 1.

After removing the solvent by evaporation, the crystal obtained was recrystallized from carbon tetrachloride to isolate 5.1 g of the II-A isomer.

EXAMPLE 7

(A) Synthesis of 3-(4-chlorophenyl)-1-(1-methylcyclopropyl)-2-(1,2,4-triazole-1-yl)-2-propene-1-one (Compound No. 29') by Method C 1-(1-Methylcyclopropyl)-2-(1,2,4-triazole-1-yl)ethane-1-one (10 g, 0.06 mole), 4-chlorobenzaldehyde (9 g, 0.06 mole), anhydrous potassium carbonate (8 g, 0.06 mole) and acetic anhydride (100 ml) were mixed, and the mixture was heated to 100° C. for 6 hours with stirring. Precipitates in the reaction solution was removed by filtration, and the filtrate was concentrated under reduced pressure to obtain an oily product. The oily product was extracted with chloroform (300 ml), and the extract was washed with a sodium hydrogen carbonate-saturated water (300 ml). The organic layer was dried over anhydrous sodium sulfate and concentrated under reduced pressure. One drop of the residue was dissolved in acetone, and the acetone solution was gas-chromatographed under the conditions described below. Then, a peak corresponding to the II-A isomer was found at a retention time of 250 sec, and that corresponding to the II-B isomer at a retention time of 300 sec. The ratio of the both isomers was 19.1/63.5, i.e. about ⅓, as calculated from the percentage of each area.

The conditions of gas chromatography was as follows:

Apparatus: Nippon Denshi 20K gas chromatograph equipped with a FID detector

Column: Glass column of 1 m in length
  liquid phase: 5% XE-60
  carrier: Chromosorb W
Temperature (column): 181° C.
Temperature (injection): 240° C.
Carrier gas: nitrogen gas, 1 kg/cm²

The residue was dissolved in benzene (100 ml). The solution was passed through a column packed with 100 to 200 mesh silica gel (300 g) and column chromatographed with n-hexane/acetone (10:1) as a developing solvent. The fraction corresponding to each isomer was recrystallized from carbon tetrachloride to separate the two entitled geometrical isomers from each other. NMR spectrum of each isomer is shown in Table 2.
II-A isomer: 1.7 g (yield 10%)
II-B isomer: 6.7 g (yield 38%)

(B) Synthesis of the starting material, 1-(1-methylcyclopropyl)-2-(1,2,4-triazole-1-yl)ethane-1-one Bromine (28 g) was added to a mixture of methyl 1-methylcyclopropyl ketone [28 g; a well-known compound in Bull. Soc. Chim. Fr., 1708 (1960)], potassium chlorate (5.8 g) and water (70 ml) at 40° to 50° C. over 4 hours with violent stirring, and then the reaction solution was stirred at room temperature for 2 hours. Thereafter, the reaction solution was extracted with two 200-ml portions of ether, and the organic layer was dried over calcium chloride and concentrated under reduced pressure to obtain 53 g of a crude product, 1-(1-methylcyclopropyl)-2-bromoethane-1-one.

A mixture of 1,2,4-triazole (18.3 g), anhydrous potassium carbonate (37 g) and acetonitrile (250 ml) was heated under reflux for 1 hour and cooled to 60° C. The crude 1-(1-methylcyclopropyl)-2-bromoethane-1-one (53 g) obtained above was added thereto over 2 hours, followed by stirring at room temperature overnight. Precipitates in the reaction solution was removed by filtration, and the filtrate was concentrated under reduced pressure. The residue obtained was extracted with addition of water (100 ml) and chloroform (300 ml), and the organic layer was dried over anhydrous magnesium sulfate and concentrated under reduced pressure. The oily residue obtained was crystallized from petroleum ether (100 ml) to obtain 27 g of 1-(1-methylcyclopropyl)-2-(1,2,4-triazole-1-yl)ethane-1-one (yield, 57% based on methyl 1-methylcyclopropyl ketone; m.p. 57°-60° C.).

EXAMPLE 8

Synthesis of the II-A isomer of 3-(4-chlorophenyl)-1-(1-methylcyclopropyl)-2-(1,2,4-triazole-1-yl)-2-propene-1-one from the II-B isomer thereof by Method C The II-B isomer (4 g) of 3-(4-chlorophenyl)-1-(1-methylcyclopropyl)-2-(1,2,4-triazole-1-yl)-2-propene-1-one obtained in Example 7 was dissolved in acetone (500 ml) and isomerized at 45° C. for 2 hours by means of a ultraviolet ray generator equipped with a 500-W high pressure mercury lamp. The ratio of II-A isomer to II-B isomer was measured by gas chromatography under the same manner as in Example 7. It was found that the ratio was 81.2 to 18.1. The reaction solution was concentrated under reduced pressure to obtain 3.9 g of crystals. The crystals were recrystallized from carbon tetrachloride to obtain 2.8 g (yield 70%) of the II-A isomer.

EXAMPLE 9

Synthesis of the II-A isomer of 3-(4-chlorophenyl)-1-(1-methylcyclopropyl)-2-(1,2,4-triazole-1-yl)-2-propene-1-one from a mixture of the geometrical isomers thereof The reaction mixture (3 g) comprising the II-A and II-B isomers (II-A/II-B=⅓) obtained in Example 7 was irradiated with ultraviolet rays for 1.5 hours in the same conditions as in Example 8. Thereafter, the ratio of the II-A isomer to II-B isomer was measured by gas chromatography. It was found that the ratio changed from ⅓ to 7/3. After removing the solvent by evaporation, the crystal obtained was recrystallized from carbon tetrachloride to obtain 1.5 g of the II-A isomer.

EXAMPLE 10

Synthesis of the II-B isomer of 1-(4-chlorophenyl)-2-(1,2,4-triazole-1-yl)-1-heptene-3-one (Compound No. 22) by Method D To a mixture of 2-hexanone (50 g) and methanol (300 ml) was added bromine (80 g) at 0° C., and the mixture was kept at 10° C. for 2 hours. Water (200 ml) and conc. sulfuric acid (50 g) were added thereto, and after stirring for 16 hours, water (500 ml) was added thereto. The reaction mixture was transferred to a separating funnel and extracted with ether (500 ml). The organic layer was washed with a 5% aqueous potassium carbonate solution and dried over calcium chloride. The solvent was then removed under reduced pressure to obtain 89 g of crude 1-bromo-2-hexanone as an oily product.

A mixture of triazole (35 g), anhydrous potassium carbonate (69 g) and acetonitrile (300 ml) was heated under reflux for 1 hour, and allowed to cool to 50° C. The crude 1-bormo-2-hexanone (89 g) obtained above was added dropwise to the mixture which was then stirred at room temperature for 16 hours. Precipitates in the reaction solution was removed by filtration, and solvent was removed under reduced pressure. To the residue obtained were added water (200 ml) and chloroform (200 ml), and the mixture was transferred to a separating funnel, followed by extraction. The organic layer was dried over anhydrous magnesium sulfate, and the solvent was removed under reduced pressure to obtain 77 g of crude 1-(1,2,4-triazolyl)-2-hexanone as an oily product.

The resulting 1-(1,2,4-triazolyl)-2-hexanone (20 g), anhydrous potassium carbonate (20 g), p-chlorobenzaldehyde (20 g) and acetic anhydride (200 ml) were mixed and heated to 90° C. for 5 hours. The reaction mixture was then concentrated under reduced pressure, and then the residue was dissolved in ethyl acetate (500 ml) and transferred to a separating funnel. The ethyl acetate solution was washed with a potassium carbonate-saturated water (200 ml), and the organic layer was separated. The solvent was removed from the organic layer under reduced pressure, and the residue was placed on a silica gel column (0.5 kg of 100 to 200 mesh silica gel) and column chromatographed with a n-hexane/acetone (10:1) mixture as a developing solvent. Thus, 3.7 g of the II-B isomer (m.p. 117°-120° C.) of 1-(4-chlorophenyl)-2-(1,2,4-triazole-1-yl)-1-heptene-3-one and 9 g of 1-(4-chlorophenyl)-2-(1,2,4-triazole-1-yl)-3-acetoxy-1,3-heptadiene (m.p. 112°-113° C.) were obtained.

To the resulting 1-(4-chlorophenyl)-2-(1,2,4-triazole-1-yl)-3-acetoxyl-1,3-heptadiene (9 g) was added conc. hydrochloric acid (100 ml), and the mixture was heated to 50° C. for 2 hours and poured into ice water (500 ml). The aqueous liquor was neutralized with potassium carbonate and extracted with ethyl acetate (300 ml). The organic layer was dried over anhydrous magnesium sulfate, and the solvent was removed by evaporation. The crystalline residue was recrystallized from a carbon tetrachloride/n-hexane (1:1) mixture to obtain 6 g of the II-B isomer of 1-(4-chlorophenyl)-2-(1,2,4-triazole-1-yl)-1-heptene-3-one.

EXAMPLE 11

Synthesis of the I-A isomer of 1-(2,4-dichlorophenyl)-2-(1,2,4-triazole-1-yl)-4,4-dimethyl-1-pentene-3-ol (Compound No. 2)

First step (condensation) Method D.

A mixture of α-(1,2,4-triazole-1-yl)-pinacolone (200 g), 2,4-dichlorobenzaldehyde (220 g) and acetic anhydride (700 cc) was heated to 50° C., and triethylamine (255 g) was added thereto. After keeping the temperature at 70° C. for 7 hours, acetic anhydride was removed under reduced pressure. Water (3 liters) was added to the residue, and the resulting crystals were collected by filtration, washed with water an dried. The crude product obtained was recrystallized from ethanol (600 cc) to obtain 304 g of the II-B isomer of 1-(2,4-dichlorophenyl)-2-(1,2,4-triazole-1-yl)-4,4-dimethyl-1-pentene-3-one (Compound No. 2').

Second step (Photoisomerization) Method C.

The II-B isomer (300 g) of Compound No. 2' obtained in the first step was dissolved in acetone (2 liters) and isomerized at 30° C. for 26 hours by means of a ultraviolet ray generator equipped with a 500-W high-pressure mercury lamp. The solvent was then removed under reduced pressure to obtain 300 g of an oily product. It was found by gas chromatography that this product was a mixture comprising 75% of the II-A isomer of Compound No. 2' and 25% of the II-B isomer of the same compound. This product was transferred to the next step without separating each isomer.

Third step (Reduction) Method A.

The mixture (300 g) of the geometrical isomers of Compound No. 2' obtained in the second step was suspended in methanol (1 kg), and sodium borohydride (38 g) was added thereto in portions while cooling the reaction mixture to 10° C. After stirring at room temperature for 1 hour, the reaction solution was concentrated under reduced pressure. The residue obtained was extracted with addition of 10% aqueous acetic acid solution (2 liters) and ethyl acetate (3 liters). The separated organic layer was washed with 5% aqueous potassium carbonate solution (1 liter) and dried over anhydrous magnesium sulfate (100 g). After removing the drying agent by filtration, the solvent was removed under reduced pressure to obtain 280 g of a crude product as crystals. This product was a mixture of the I-A and I-B isomers of Compound No. 2 (mixing ratio: I-A/I-B=75/25). The crude product (280 g) was recrystallized from carbon tetrachloride (600 cc) to obtain 209 g of the entitled compound (I-A isomer of Compound No. 2). The mother liquor from recrystallization was concentrated to a half to obtain 25 g of the I-B isomer of Compound No. 2 as secondary crystal.

The II-A isomers of the ketone compound (II) obtained by Methods C and D are shown in Table 2 together with the II-B isomers. NMR spectrum in the table is indicated in the same form as in Table 1.

TABLE 2

| | | | | | | NMR spectrum | |
|---|---|---|---|---|---|---|---|
| | | | | | | Olefin proton | |
| Compound No. | $R_2$ | $(R_3)_n$ | Kind of geometrical isomer | Physical constant | Triazole proton | —CH=C—C(=O)— | NMR spectrum $R_2$ proton |
| 1' | $C(CH_3)_3$ | 4-Cl | II-A | mp 108–109° C. | 8.11, 7.90 | 6.99 | 0.99 |
| | | | II-B | mp 78–79° C. | 8.14, 7.98 | 7.49 | 1.22 |
| 2' | $C(CH_3)_3$ | 2,4-di-Cl | II-A | mp 92–93° C. | 8.30, 8.40 | 7.22 | 0.97 |
| | | | II-B | mp 119–120° C. | 7.94, 7.80 | 7.46 | 1.27 |
| 3' | $C(CH_3)_3$ | 4-Br | II-A | mp 129–131° C. | 8.25, 8.05 | 7.12 | 1.02 |
| | | | II-B | mp 93–94° C. | 8.02, 7.86 | 7.38 | 1.17 |
| 4' | $C(CH_3)_3$ | 4-F | II-A | mp 69–71° C. | 8.28, 8.06 | 7.47–6.92 (m) *1 | 1.00 |
| | | | II-B | $n_D^{24.5}$ 1.5568 | 8.08, 7.94 | 7.48 | 1.21 |
| 5' | $C(CH_3)_3$ | 2-Cl | II-A | mp 93–95° C. | 8.34, 8.04 | 7.45–7.20 (m) *1 | 0.93 |
| | | | II-B | mp 62–64° C. | 8.08, 7.91 | 7.68 | 1.30 |
| 6' | $C(CH_3)_3$ | 4-phenyl | II-A | mp 185–186° C. | 8.30, 8.09 | 7.22 | 1.05 |
| | | | II-B | mp 111–112° C. | 8.06, 7.91 | 7.51 | 1.21 |
| 7' | $C(CH_3)_3$ | 4-OCH$_3$ | II-A | mp 112–113° C. | 8.22, 8.01 | 7.08 | 1.03 |
| | | | II-B | *3 | 8.20, 8.06 | 7.64 | 1.24 |
| 8' | $C(CH_3)_3$ | 4-CN | II-A | mp 110–113° C. | 8.30, 8.08 | 7.21 | 1.01 |
| | | | II-B | mp 114–115° C. | 8.15, 7.99 | 7.45 | 1.23 |
| 9' | $C(CH_3)_3$ | H | II-A | mp 73–74° C. | 8.26, 8.03 | 7.16 | 1.00 |
| | | | II-B | mp 62–64° C. | 8.20, 8.03 | 7.60 | 1.24 |
| 10' | $C(CH_3)_3$ | 4-CH$_3$ | II-A | mp 87–88° C. | 8.30, 8.07 | 7.15 | 1.02 |
| | | | II-B | $n_D^{22}$ 1.5607 | 8.13, 7.95 | 7.56 | 1.22 |
| 11' | $C(CH_3)_3$ | 4-NO$_2$ | II-A | mp 114–116° C. | 8.28, 8.19 | 7.24 | 1.00 |
| | | | II-B | mp 65–68° C. | 8.20, 8.15 | 7.54 | 1.25 |
| 12' | $C(CH_3)_3$ | 4-phenoxy | II-A | mp 100–101° C. | 8.20, 8.00 | 7.40–6.82 (m) *1 | 1.02 |

TABLE 2-continued

Structure:

$(R_3)_n$-C₆H₄-CH=C(N(1H,m)-triazole)-C(=O)-R₂

| Compound No. | R₂ | (R₃)ₙ | Kind of geometrical isomer | Physical constant | Triazole proton | Olefin proton —CH=C—C(=O)— | NMR spectrum R₂ proton |
|---|---|---|---|---|---|---|---|
| 13' | CH₃ | 4-Cl | II-B | *3 | 8.20, 7.98 | 7.55 | 1.22 |
|  |  |  | II-A | mp 38–41° C. | 8.39, 8.08 | 7.40 | 2.22 |
|  |  |  | II-B | mp 124–126° C. | 8.21, 8.06 | 7.76 | 2.28 |
| 14' | -CH(CH₂-CH₂) (cyclopropyl) | 4-Cl | II-A | $n_D^{24}$ 1.6060 | 8.35, 8.05 | 7.52 | 2.00–1.65 (1H, m), 1.45–1.10 (2H, m), 1.10–0.75 (2H, m) |
|  |  |  | II-B | mp 122–125° C. | 8.20, 8.07 | 7.79 | 2.05–1.70 (1H, m), 1.35–0.80 (4H, m) |
| 15' | -CH(CH₃)₂ | 4-Cl | II-A | mp 76–78° C. | 8.32, 8.06 | 7.43 | 2.65 (1H, m), 1.09 (6H, d, J=7 Hz) |
|  |  |  | II-B | mp 100–101° C. | 8.20, 8.04 | 7.76 | 2.97 (1H, m), 1.15 (6H, d, J=7 Hz) |
| 16' | C(CH₃)₃ | 3-CF₃ | II-A | $n_D^{25}$ 1.5181 | 8.27, 8.07 | 7.20 | 1.00 |
|  |  |  | II-B | $n_D^{25}$ 1.5205 | 8.12, 8.95 | 7.52 | 1.22 |
| 17' | C(CH₃)₃ | 3-F—4-OCH₃ | II-A | mp 116–117° C. | 8.25, 8.03 | 7.18–6.90 (m) *1 | 1.06 |
|  |  |  | II-B | $n_D^{26}$ 1.5611 | 8.23, 8.08 | 7.58 | 1.24 |
| 18' | C(CH₃)₃ | 2-Cl—5-NO₂ | II-A | mp 131–134° C. | 8.37, 8.22–8.05 (m) *2 | 7.28 | 1.00 |
|  |  |  | II-B | mp 121–122° C. | 8.06, 8.02 | 7.53 | 1.29 |
| 19' | C(CH₃)₃ | 2-OCH₃ | II-A | mp 89.4° C. | 8.28, 7.97 | 7.26 | 1.00 |
|  |  |  | II-B | *3 | 8.03, 7.89 | 7.95 | 1.27 |
| 20' | -CH(CH₂CH₃)(CH₃) | 4-Cl | II-A | mp 55.5–56° C. | 8.27, 7.97 | 7.36 | 2.40 (1H, m), 1.44 (2H, m), 1.00 (3H, d, J=7 Hz), 0.77 (3H, t, J=6 Hz) |
|  |  |  | II-B | mp 59.5–60° C. | 8.15, 7.98 | 7.70 | 2.75 (1H, m), 1.50 (2H, m), 1.14 (3H, d, J=7 Hz), 0.87 (3H, m), t, J=7 Hz) |
| 21' | —(CH₂)₃CH₃ | 4-Cl | II-A | mp 65–67° C. | 8.30, 8.01 | 7.30 | 2.49 (2H, t, J=7 Hz), 1.90–1.00 (4H, m), 0.83 (3H, t, J=6 Hz) |
|  |  |  | II-B | mp 117–120° C. | 8.20, 8.04 | 7.75 | 2.53 (2H, t, J=7 Hz), 1.90–1.00 (4H, m), 0.90 (3H, t, J=6 Hz) |
| 22' | C(CH₃)₃ | 2,3-di-Cl | II-A | mp 81–82° C. | 8.35, 8.08 | 7.40–7.15 (m) *1 | 0.98 |
|  |  |  | II-B | mp 83–84° C. | 8.09, 7.95 | 7.60 | 1.29 |
| 23' | —(CH₂)₅CH₃ | 4-Cl | II-A | $n_D^{23.5}$ 1.5616 | 8.26, 7.98 | 7.28 | 2.46 (2H, t, J=8 Hz), 1.80–1.00 (8H, m), 0.85 (3H, t, J=5 Hz) |
|  |  |  | II-B | mp 60–62° C. | 8.16, 7.98 | 7.70 | 2.52 (2H, t, J=7 Hz), 2.00–1.00 (8H, m), 0.88 (3H, t, J=5 Hz) |
| 24' | C(CH₃)₃ | 4-CH(CH₃)₂ | II-A | mp 59–62° C. | 8.27, 8.03 | 7.09 | 1.01 |
|  |  |  | II-B | $n_D^{24}$ 1.5572 | 8.17, 8.00 | 7.60 | 1.20 |
| 25' | CH₂CH(CH₃)₂ | 4-Cl | II-A | mp 78–80° C. | 8.34, 8.05 | 7.28 | 2.50–2.00 (3H, m), 0.87 (6H, d, J=7 Hz) |
|  |  |  | II-B | mp 86–87° C. | 8.18, 7.99 | 7.71 | 2.60–2.00 (3H, m), 0.95 (6H, J=6 Hz) |
| 26' | C(CH₃)₃ | 4-OC₂H₅ | II-A | *3 | 8.20, 7.99 | 7.30–6.70 (m) *1 | 1.00 |
|  |  |  | II-B | mp 82–83° C. | 8.18, 8.01 | 7.63 | 1.22 |
| 27' | CH₂CH₂CH₃ | 4-Cl | II-A | $n_D^{24}$ 1.5693 | 8.31, 8.05 | 7.35 | 2.45 (2H, t, J=7 Hz), 1.90–1.30 (2H, m), 0.85 (3H, t, J=7 Hz) |
|  |  |  | II-B | mp 110–111° C. | 8.20, 8.11 | 7.72 | 2.50 (2H, t, J=7 Hz), 2.00–1.40 (2H, m), 0.92 (3H, t, J=7 Hz) |

TABLE 2-continued

Structure: (R₃)ₙ-phenyl-CH=C(-NH-triazole)(1H,m)-C(=O)-R₂

| Compound No. | R₂ | (R₃)ₙ | Kind of geometrical isomer | Physical constant | Triazole proton | Olefin proton —CH=C—C(=O)— | NMR spectrum R₂ proton |
|---|---|---|---|---|---|---|---|
| 28' | —CH(CH₃)(CH₂CH₃) | 2,4-di-Cl | II-A | $n_D^{24}$ 1.5787 | 8.32, 8.06 | 7.59–7.20 (m) *1 | 2.50–2.00 (1H, m), 1.80–1.20 (2H, m), 1.01 (3H, d, J=7 Hz), 0.78 (3H, t, J=7 Hz) |
|  |  |  | II-B | mp 88–89° C. | 8.12, 7.99 | 7.99 | 3.10–2.50 (1H, m), 1.90–1.40 (2H, m), 1.20 (3H, d, J=7 Hz), 0.92 (3H, t, J=7 Hz) |
| 29' | —C(CH₃)(CH₂CH₂) (cyclopropyl) | 4-Cl | II-A | 89–92° C. | 8.28, 8.07 | 7.19 | 1.45–1.15 (2H, m), 1.25 (3H, S), 0.99–0.75 (2H, m) |
|  |  |  | II-B | mp 74–75° C. | 8.12, 8.03 | 7.55 | 1.50–1.25 (2H, m), 1.28 (3H, S), 0.90–0.65 (2H, m) |
| 30' | —C(CH₃)(CH₂CH₂) | 2,4-di-Cl | II-A | 81–83° C. | 8.25, 8.05 | 7.48–7.20 (m) *1 | 1.45–1.15 (2H, m), 1.21 (3H, S), 0.95–0.70 (2H, m) |
|  |  |  | II-B | mp 89–90° C. | 8.10 (2H, S) | 7.76 | 1.50–1.30 (2H, m), 1.34 (3H, S), 0.97–0.75 (2H, m) |
| 31' | —C(CH₃)(CH₂CH₂) | 4-Br | II-A | mp 88–89° C. | 8.27, 8.02 | 7.14 | 1.55–1.15 (2H, m), 1.23 (3H, S), 1.10–0.75 (2H, m) |
|  |  |  | II-B | mp 73–74° C. | 8.16, 8.05 | 7.56 | 1.50–1.21 (2H, m), 1.28 (3H, S), 0.90–0.65 (2H, m) |
| 32' | —C(CH₃)(CH₂CH₂) | 4-F | II-A | $n_D^{27}$ 1.5683 | 8.38, 8.07 | 7.40–6.90 (m) *1 | 1.40–1.20 (2H, m), 1.25 (3H, S), 0.98–0.70 (2H, m) |
|  |  |  | II-B | $n_D^{26}$ 1.5662 | 8.15, 8.05 | 7.61 | 1.45–1.15 (2H, m), 1.29 (3H, S), 0.90–0.65 (2H, m) |
| 33' | —C(CH₃)(CH₂CH₂) | H | II-A | $n_D^{27}$ 1.5842 | 8.30, 8.09 | 7.26 | 1.50–1.20 (2H, m), 1.25 (3H, S), 0.95–0.75 (2H, m) |
|  |  |  | II-B | $n_D^{26}$ 1.5849 | 8.14, 8.03 | 7.65 | 1.50–1.25 (2H, m), 1.31 (3H, S), 0.90–0.68 (2H, m) |
| 34' | —C(CH₃)₃ | 3,5-di-Cl | II-A | $n_D^{20}$ 1.5785 | 8.23, 8.04 | 7.05 | 1.03 |
|  |  |  | II-B | mp 107–108° C. | 8.32, 8.14 | 7.50 | 1.26 |
| 35' | —C(CH₃)₃ | 4-C₂H₅ | II-A | mp 77–78° C. | 8.25, 8.00 | 7.09 | 1.01 |
|  |  |  | II-B | mp 93–94° C. | 8.13, 7.97 | 7.59 | 1.20 |
| 36' | —C(CH₃)₃ | 2-F—4-Cl | II-A | mp 107–108° C. | 8.31, 8.05 | 7.30–6.97 (m) *1 | 1.00 |
|  |  |  | II-B | mp 71–72° C. | 8.11, 8.01 | 7.56 | 1.25 |
| 37' | —(CH₃)₃ | 3,4,5-tri-OCH₃ | II-A | $n_D^{20}$ 1.5575 | 8.31, 8.06 | 7.11 | 1.01 |
|  |  |  | II-B | mp 103° C. | 8.19, 8.06 | 7.58 | 1.24 |

Note:
*1 Olefin proton and phenyl proton appear at the same position.
*2 Triazole proton and phenyl proton appear at the same position.
*3 Resinous product In the practical application of the present compounds thus obtained, they may be used alone without other components or in a mixture with carriers for the ease of use as a fugicide, herbicide and plant growth regulator. The commonly used preparation forms include for example dusts, wettable powders, oil sprays, emulsifiable concentrates, tablets, granules, fine granules, aerosols and flowable preparations.

The foregoing preparations generally contain 0.1 to 95.0% by weight of active ingredient (including other ingredients mixed). A suitable amount of active ingredient applied is generally 2 to 500 g per 10 are, and the concentration of active ingredient applied is preferably within a range of 0.001 to 1.0%. Since, however, the amount and concentration depend upon the preparation forms, application times, application techniques, application sites, diseases and crops, they may properly be increased or decreased irrespective of the aforesaid ranges.

In formulating the fungicide, herbicide and plant growth regulator of the present invention, suitable solid carriers or liquid carriers are blended. As the solid carriers, there may be given for example inorganic substances (e.g. clays represented by kaolinite group, montmorillonite group or attapulgite group, talc, mica, pyrophyllite, pumice, vermiculite, gypsum, calcium carbonate, dolomite, diatomaceous earth, magnesium, lime, apatite, zeolite, silicic acid anhydride, synthetic calcium silicate), vegetable organic substances (e.g. soybean powder, tobacco powder, walnut powder, flour, wooden powder, starch, crystalline cellulose), synthetic or natural high molecular weight compounds (e.g. coumarone resins, petroleum resin, alkyd resin, polyvinyl chloride, polyalkylene glycol, ketone resin, ester gum, copal gum, dammar gum), and waxes (e.g. carnauba wax, bees wax), and urea.

As the liquid carriers, there may be given for example paraffin or naphthalne hydrocarbons (e.g. kerosene, mineral oil, spindle oil, white oil), aromatic hydrocarbons (e.g. benzene, toluene, xylene, ethylbenzene, cumene, methylnaphthalene), halogenated hydrocarbons (e.g. carbon tetrachloride, chloroform, trichloroethylene, monochlorobenzene, o-chlorotoluene), ethers (e.g. dioxane, tetrahydrofuran), ketones (e.g. acetone, methyl ethyl ketone, diisobutyl ketone, cyclohexanone, acetophenone, isophorone), esters (e.g. ethyl acetate, amyl acetate, ethylene glycol acetate, diethylene glycol acetate, dibutyl maleate, diethyl succinate), alcohols (e.g. methanol, n-hexanol, ethylene glycol, diethylene glycol, cyclohexanol, benzyl alcohol), ether alcohols (e.g. ethylene glycol ethyl ether, ethylene glycol phenyl ether, diethylene glycol ethyl ether, diethylene glycol butyl ether), polar solvents (e.g. dimethylformamide, dimethyl sulfoxide) and water.

As surfactants used for emulsification, dispersion, wetting, spreading, binding, regulation of disintegration, stabilization of active ingredient, flowability improvement and anti-corrosion, any one of nonionic, anionic, cationic and amphoteric surfactants may be used, but generally nonionic and/or anionic ones are used. As suitable nonionic surfactants, there may be given for example those obtained by polymerizing ethylene oxide and a higher alcohol (e.g. lauryl alcohol, stearyl alcohol, oleyl alcohol), ethylene oxide and an alkylphenol (e.g. isooctylphenol, nonylphenol), ethylene oxide and an alkylnaphthol (e.g. butylnaphthol, octylnaphthol), ethylene oxide and a higher fatty acid (e.g. palmitic acid, stearic acid, oleic acid), ethylene oxide and a mono- or di-alkyl phosphate (e.g. stearyl phosphate, dilauryl phosphate), or ethylene oxide and an amine (e.g. dodecylamine, stearic acid amide), higher fatty acid esers of a polyhydric alcohol (e.g. sorbitan) and those obtained by polymerizing said esters and ethylene oxide, and ethylene oxide/propylene oxide polymers. As suitable anionic surfactants, there may be given for example salts of an alkyl sulfate (e.g. sodium lauryl sulfate, amine salts of oleyl sulfate), alkylsulfonates (e.g. sodium salt of dioctyl sulfosuccinate, sodium 2-ethylhexenesulfonate) and arylsulfonates (e.g. sodium isopropylnaphthalenesulfonate, sodium methylenebisnaphthalenesulfonate, sodium lignosulfonate, sodium dodecyclbenzenesulfonate).

Further, the preparations of the present compound may contain high molecular weight compounds and other assistants, in order to improve their performances and biological activity. The high molecular weight compounds include for example casein, gelatin, albumin, glue, sodium alginate, carboxymethyl cellulose, methyl cellulose, hydroxyethyl cellulose and polyvinyl alcohol.

The foregoing carriers and assistants are properly used alone or in combination according to intended uses, taking into account preparation forms and application techniques.

The content of active ingredient in the dusts is generally 1 to 25 percent by weight, and the rest is a solid carrier.

As to the wettable powders, the content of active ingredient is generally 25 to 90 percent by weight. The rest is a solid carrier and a dispersion-wetting agent, and if necessary a protective colloid, a thixotropic agent and an anti-foaming agent are added thereto.

As to the granules, the content of active ingredient is generally 1 to 35 percent by weight, and the remainder is a solid carrier. The active ingredient is uniformly mixed with a solid carrier, or it is uniformly fixed or adsorbed to the surface of the solid carrier. The particles are about 0.2 mm to about 1.5 mm in diameter.

As to the emulsifiable concentrates, the content of active ingredient is generally 5 to 30 percent by weight, an emulsifier occupies about 5 to about 20 percent by weight, and the rest is a liquid carrier. If necessary, anticorrosion agents are added.

Further, the compounds of the present invention may be applied in a mixture with other fungicides, herbicides and plant growth regulators without lowering the controlling effect of each active ingredient of the mixture. As the fungicides, there may be given N-(3,5-dichlorophenyl)-1,2-dimethylcyclopropane-1,2-dicarboximide, S-n-butyl S-p-tert-butylbenzyldithiocarbonimidate, O,O-dimethyl O-(2,6-dichloro-4-methylphenyl)phosphorothioate, methyl 1-butylcarbamoyl-1H-benzimidazole-2-yl-carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylene-bis(dithiocarbamate), zinc dimethylthiocarbamate, manganese ethylene-bis(dithiocarbamate), bis(N,N-dimethylthiocarbamoyl)disulfide, tetrachloroisophthalonitrile, 8-hydroxyquinoline, dodecylguanidine acetate, 5,6-dihydro-2-methyl-1,4-oxathiine-3-carboxanilide, N'-dichlorofluoromethylthio-N,N-dimethyl-N'-phenylsulfamide, 1-(4-chlorophenoxy)-3,3-dimethyl-1-(1,2,4-triazole-1-yl)-2-butanone, 1,2-bis(3-methoxycarbonyl-2-thioureido)-benzene, methyl N-(2,6-dimethylphenyl)-N-methoxyacetyl-2-methylglycinate, aluminum ethylphosphite and the like. As the herbicides, there may be given phenoxy series herbicides such as 2,4-dichlorophenoxyacetic acid, 2-methyl-4-chlorophenoxyacetic acid, 2-methyl-4-chlorophenoxybutyric acid and 2-methyl-4-chlorophenoxyacetic acid (including esters and salts); diphenyl ether series herbicides such as 2,4-dichlorophenyl 4'-nitrophenyl ether, 2,4,6-trichlorophenyl 4'-nitrophenyl ether, 2-chloro 4trifluoromethylphenyl 3'-ethoxy-4'-nitrophenyl ether, 2,4-dichlorophenyl 4'-nitro-3'-methoxyphenyl ether and 2,4-dichlorophenyl 3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; urea series herbicides such as 3-(3,4-dichlorophenyl)-1,1,-dimethylurea, 3-(3,4-dichlorophenyl)-1-methoxy-1-methylurea, 1-(α,α-dimethylbenzyl)-3-p-tolylurea and 1-(2-benzothiazolyl)-1,3-dimethylurea; carbamate series herbicides such as isopropyl N-(3-chlorophenyl)-carbamate and methyl N-(3,4-dichlorophenyl)carbamate; thiolcarbamate series herbicides such as S-(4-chlorobenzyl) N,N-diethylthiolcarbamate and S-ethyl N,N-hexamethylenetiolcarbamate; acid anilide series herbicides such as 3,4-dichloropropionanilide, 2-chloro-N-methoxymethyl-2',6'-diethylacetanilide, 2-chloro-2',6'-diethyl-N-(butoxymethyl)acetanilide, 2-chloro-2',6'-diethyl-N-(n-propoxyethyl)acetanilide and N-chloroacetyl-N-(2,6-diethylphenyl)glycine ethyl ester; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bipyridinium chloride; phosphorus series herbicides such as N-(phosphonomethyl)glycine, N,N-bis(phosphonomethyl)glycine, O-ethyl O-(2nitro-5-methylphenyl) N-sec-butyl phosphoroamidothioate, S-(2-methyl-1-piperidylcarbonylmethyl) O,O-di-n-propyldithiophosphate and S-(2-methyl-1-piperidylcarbonylmethyl) O,O-diphenyldithiophosphate; toluidine series herbicides such as α,α,α-trifluoro-2,6-dinitro-N,N-dipropyl-p-toluidine; 5-tert-butyl-3-(2,4-dichloro-5-isopropoxyphenyl)-1,3,4-oxadiazolin-2-one; 3-isopropyl-(1H)-2,1,3-benzothiadiazine-(3H)-one-2,2-dioxide; α-(β-naphthoxy)propionanilide; 4-(2,4-dichlorobenzoyl)-1,3-dimethylpyrazole-5yl p-toluenesulfonate; 3-(methoxycarbonylamino)phenyl 3-methylphenylcarbamate; 4-amino-3-methyl-6-phenyl-1,2,4-triazine and the like.

Also, the compounds of the present invention may be applied in a mixture with other insecticides without lowering the controlling effect of each active ingredient of the mixture. As the insecticides, there may be given organo-phosphorus insecticides such as O,O-dimethyl O-(4-nitro-3-methylphenyl)phosphorothioate, O-(4-cyanophenyl) O,O-dimethylphosphorothioate, O-(4-cyanophenyl) O-ethylphenylphosphonothioate, O,O-dimethyl S-(N-methylcarbamoylmethyl)phosphorodithioate, 2-methoxy-4H-1,3,2-benzodioxaphosphorine-2-sulfide and O,O-dimethyl S-(1-ethoxycarbonyl-1-phenylmethyl)phosphorodithioate; and pyrethroid series insecticides such as α-cyano-3-phenoxybenzyl 2-(4-chlorophenyl)isovalerate, 3-phenoxybenzyl 2,2-dimethyl-3-(2,2-dichlorovinyl)cyclopropanecarboxylate and α-cyano-3-phenoxybenzyl 2,2-dimethyl-3-(2,2-dibromovinyl)cyclopropanecarboxylate. Consequently, two kinds or more of disease and pest can be controlled at the same time, and further a synergistic effect owing to mixing is expected.

Next, the usefulness of the present compounds as fungicides, herbicides and plant growth regulators for agriculture and horticulture will be illustrated more clearly with reference to the following test examples and preparation examples.

TEST EXAMPLE 1

Fungitoxic Effect

A medium containing 5 g of polypeptone, 20 g of malt extract, 20 g of sucrose and 20 g of agar per 1 liter of water, was turned into a solution by heating. The aqueous dilute liquor of the emulsifiable concentrate of each test compound was added thereto so that the concentration of the test compound in the medium was a predetermined one. After thoroughly stirring the medium, the medium was poured into a glass Petri dish to make an agar plate. After the agar solidified, it was inoculated with the mycelial disc or spore suspension of a test fungus. The name of the test fungus and a culture period from inoculation to observation are as shown below. The culture temperature was 20° C. for *Venturia inaequalis* and 28° C. for other fungi.

| Name of fungus | Abbreviation | Culture period |
|---|---|---|
| *Helminthosporium gramineum* | Hg | 6 days |
| *Penicillium italicum* | Pi | 6 days |
| *Venturia inaequalis* | Vi | 7 days |
| *Valsa mali* | Vm | 4 days |
| *Mycosphaerella melonis* | Mm | 4 days |
| *Diaporthe citri* | Dc | 6 days |
| *Ustilago nuda* | Un | 6 days |
| *Verticillium albo-atrum* | Va | 7 days |
| *Septoria tritici* | St | 7 days |
| *Cercospora beticola* | Cb | 7 days |
| *Fusarium oxysporum* f. sp. *lycopersici* | Fo | 4 days |
| *Alternaria kikuchiana* | Ak | 4 days |

The degree of growth inhibition of the test compounds was evaluated in four ratings A, B, C and D:

| A: Degree of growth inhibition | 100% |
|---|---|
| B: Degree of growth inhibition | 90% or more |
| C: Degree of growth inhibition | 89–50% |
| D: Degree of growth inhibition | 40% or less |

As shown in Table 3, it was found that the I-A isomer of the present invention has a markedly broad antimicrobial spectrum as well as a remarkably high activity as compared with the I-B, II-A and II-B isomers.

TABLE 3

| Test Compound No. | Concentration of active ingredient (ppm) | Degree of growth inhibition | | | | | | | | | | | |
|---|---|---|---|---|---|---|---|---|---|---|---|---|---|
| | | Hg | Pi | Vi | Vm | Mm | Dc | Un | Va | St | Cb | Fo | Ak |
| I-A isomer of Compound 1 | 5 | A | A | A | A | A | A | B | A | A | A | — | — |
| I-A isomer of Compound 2 | " | A | A | A | A | A | A | C | C | A | A | — | — |
| I-A isomer of Compound 3 | " | A | A | A | A | A | A | C | A | A | A | — | — |
| I-A isomer of Compound 4 | " | B | A | C | C | C | A | C | C | C | A | — | — |
| I-A isomer of Compound 5 | " | A | A | A | A | A | B | C | C | A | A | — | — |
| I-A isomer of Compound 6 | " | C | B | A | A | C | B | C | C | A | C | — | — |
| I-A isomer of Compound 7 | " | B | A | A | C | A | B | C | C | A | B | — | — |
| I-A isomer of Compound 8 | " | B | B | B | C | C | B | C | C | C | B | — | — |
| I-A isomer of Compound 9 | " | B | B | A | C | B | B | C | C | A | A | — | — |
| I-A isomer of Compound 10 | " | A | A | A | B | A | B | C | C | A | B | — | — |
| I-A isomer of Compound 11 | " | B | B | B | C | B | B | C | C | C | B | — | — |

TABLE 3-continued

| Test Compound No. | Concentration of active ingredient (ppm) | Degree of growth inhibition | | | | | | | | | | | |
|---|---|---|---|---|---|---|---|---|---|---|---|---|---|
| | | Hg | Pi | Vi | Vm | Mm | Dc | Un | Va | St | Cb | Fo | Ak |
| I-A isomer of Compound 12 | " | B | C | B | C | B | B | C | C | B | C | — | — |
| I-A isomer of Compound 13 | 20 | B | C | B | A | C | C | C | C | A | A | — | — |
| I-A isomer of Compound 14 | 5 | B | B | B | C | B | B | C | C | B | B | — | — |
| I-A isomer of Compound 15 | " | B | B | B | B | B | C | C | C | B | C | — | — |
| I-A isomer of Compound 16 | " | B | B | B | B | B | B | C | C | B | C | — | — |
| I-A isomer of Compound 17 | " | B | B | B | B | B | B | C | C | B | B | — | — |
| I-A isomer of Compound 18 | " | A | C | A | C | B | A | C | C | C | B | — | — |
| I-A isomer of Compound 19 | " | B | B | A | B | B | B | C | B | A | B | — | — |
| I-A isomer of Compound 20 | " | B | B | B | C | B | B | C | C | C | B | — | — |
| I-A isomer of Compound 21 | " | C | C | A | A | C | B | C | C | A | C | — | — |
| I-A isomer of Compound 22 | " | C | C | A | A | C | B | C | C | A | C | — | — |
| I-A isomer of Compound 23 | " | C | C | A | A | C | C | C | C | A | C | — | — |
| I-A isomer of Compound 24 | " | B | C | A | C | B | B | C | C | A | C | B | B |
| I-A isomer of Compound 25 | " | A | B | A | C | C | B | C | C | A | C | C | C |
| I-A isomer of Compound 26 | " | A | A | A | B | B | B | C | B | A | B | — | — |
| I-A isomer of Compound 27 | " | A | A | A | A | A | A | A | A | A | A | — | — |
| I-A isomer of Compound 28 | " | A | A | A | C | C | C | C | C | A | C | C | B |
| I-A isomer of Compound 29 | " | | | | | | | | | | | | |
| I-A isomer of Compound 30 | " | A | A | A | — | A | A | — | B | A | — | B | B |
| I-A isomer of Compound 31 | " | A | A | A | — | A | A | — | B | A | — | B | B |
| I-A isomer of Compound 32 | " | A | A | A | — | A | A | — | B | A | — | B | B |
| I-A isomer of Compound 33 | " | B | B | A | — | B | B | — | C | A | — | C | B |
| I-A isomer of Compound 34 | " | B | B | A | — | B | B | — | C | A | — | C | B |
| I-A isomer of Compound 35 | " | B | B | A | A | — | A | — | — | A | B | B | — |
| I-A isomer of Compound 40 | " | B | C | A | A | — | B | — | — | A | C | A | — |
| I-A isomer of Compound 43 (Reference compound) | " | B | C | B | A | — | B | — | — | B | C | B | — |
| I-B isomer of Compound 1 | " | D | D | D | D | D | D | D | D | D | D | — | — |
| I-B isomer of Compound 2 | " | D | D | D | D | D | D | D | D | D | D | — | — |
| I-B isomer of Compound 3 | " | D | D | D | D | D | D | D | D | D | D | — | — |
| I-B isomer of Compound 4 | " | D | D | D | D | D | D | D | D | D | D | — | — |
| I-B isomer of Compound 5 | " | D | D | D | D | D | D | D | D | D | D | — | — |
| I-B isomer of Compound 6 | " | D | D | D | D | D | D | D | D | D | D | — | — |
| I-B isomer of Compound 7 | " | D | D | D | D | D | D | D | D | D | D | — | — |
| I-B isomer of Compound 8 | " | D | D | D | D | D | D | D | D | D | D | — | — |
| I-B isomer of Compound 9 | " | D | D | D | D | D | D | D | D | D | D | — | — |
| I-B isomer of Compound 10 | " | D | D | D | D | D | D | D | D | D | D | — | — |
| I-B isomer of Compound 11 | " | D | D | D | D | D | D | D | D | D | D | — | — |
| I-B isomer of | " | D | D | D | D | D | D | D | D | D | D | — | — |

TABLE 3-continued

| Test Compound No. | Concentration of active ingredient (ppm) | Degree of growth inhibition | | | | | | | | | | | |
|---|---|---|---|---|---|---|---|---|---|---|---|---|---|
| | | Hg | Pi | Vi | Vm | Mm | Dc | Un | Va | St | Cb | Fo | Ak |
| Compound 12 I-B isomer of Compound 13 | 20 | D | D | D | D | D | D | D | D | D | D | — | — |
| I-B isomer of Compound 14 | 5 | D | D | D | D | D | D | D | D | D | D | — | — |
| I-B isomer of Compound 15 | " | D | D | D | D | D | D | D | D | D | D | — | — |
| I-B isomer of Compound 16 | " | D | D | D | D | D | D | D | D | D | D | — | — |
| I-B isomer of Compound 17 | " | D | D | D | D | D | D | D | D | D | D | — | — |
| I-B isomer of Compound 18 | " | D | D | D | D | D | D | D | D | D | D | — | — |
| I-B isomer of Compound 19 | " | D | D | D | D | D | D | D | D | D | D | — | — |
| I-B isomer of Compound 20 | " | D | D | D | D | D | D | D | D | D | D | — | — |
| I-B isomer of Compound 21 | " | D | D | D | D | D | D | D | D | D | D | — | — |
| I-B isomer of Compound 22 | " | D | D | D | D | D | D | D | D | D | D | — | — |
| I-B isomer of Compound 23 | " | D | D | D | D | D | D | D | D | D | D | — | — |
| I-B isomer of Compound 24 | " | D | D | D | D | D | D | D | D | D | D | D | D |
| I-B isomer of Compound 25 | " | D | D | D | D | D | D | D | D | D | D | D | D |
| I-B isomer of Compound 26 | " | D | D | D | D | D | D | D | D | D | D | — | — |
| I-B isomer of Compound 27 | " | D | D | D | D | D | D | D | D | D | D | — | — |
| I-B isomer of Compound 28 | " | D | D | D | D | D | D | D | D | D | D | D | D |
| I-B isomer of Compound 30 | " | D | D | D | — | D | D | — | D | D | — | D | D |
| I-B isomer of Compound 31 | " | D | D | D | — | D | D | — | D | D | — | D | D |
| I-B isomer of Compound 32 | " | D | D | D | — | D | D | — | D | D | — | D | D |
| I-B isomer of Compound 33 | " | D | D | D | — | D | D | — | D | D | — | D | D |
| I-B isomer of Compound 34 | " | D | D | D | — | D | D | — | D | D | — | D | D |
| I-B isomer of Compound 35 | " | D | D | C | C | — | D | — | — | D | D | D | — |
| I-B isomer of Compound 43 | " | D | D | D | D | — | D | — | — | D | D | D | — |
| II-A isomer of Compound 1' | " | D | D | D | D | D | D | D | D | D | D | — | — |
| II-A isomer of Compound 2' | " | D | D | D | D | D | D | D | D | D | D | — | — |
| II-A isomer of Compound 3' | " | D | D | D | D | D | D | D | D | D | D | — | — |
| II-A isomer of Compound 4' | " | D | D | D | D | D | D | D | D | D | D | — | — |
| II-A isomer of Compound 5' | " | D | D | D | D | D | D | D | D | D | D | — | — |
| II-A isomer of Compound 6' | " | D | D | D | D | D | D | D | D | D | D | — | — |
| II-A isomer of Compound 7' | " | D | D | D | D | D | D | D | D | D | D | — | — |
| II-A isomer of Compound 8' | " | D | D | D | D | D | D | D | D | D | D | — | — |
| II-A isomer of Compound 9' | " | D | D | D | D | D | D | D | D | D | D | — | — |
| II-A isomer of Compound 10' | " | D | D | D | D | D | D | D | D | D | D | — | — |
| II-A isomer of Compound 11' | " | D | D | D | D | D | D | D | D | D | D | — | — |
| II-A isomer of Compound 12' | " | D | D | D | D | D | D | D | D | D | D | — | — |
| II-A isomer of Compound 13' | 20 | D | D | D | D | D | D | D | D | D | D | — | — |
| II-A isomer of Compound 14' | 5 | D | D | D | D | D | D | D | D | D | D | — | — |
| II-A isomer of Compound 15' | " | D | D | D | C | D | D | D | D | D | D | — | — |
| II-A isomer of | " | D | D | D | D | D | D | D | D | D | D | — | — |

TABLE 3-continued

| Test Compound No. | Concentration of active ingredient (ppm) | Degree of growth inhibition |||||||||||||
|---|---|---|---|---|---|---|---|---|---|---|---|---|---|
| | | Hg | Pi | Vi | Vm | Mm | Dc | Un | Va | St | Cb | Fo | Ak |
| Compound 16' | | | | | | | | | | | | | |
| II-A isomer of Compound 17' | " | D | D | D | D | D | D | D | D | D | D | — | — |
| II-A isomer of Compound 18' | " | D | D | D | D | D | D | D | D | D | D | — | — |
| II-A isomer of Compound 19' | " | D | D | D | D | D | D | D | D | D | D | — | — |
| II-A isomer of Compound 20' | " | D | D | D | D | D | D | D | D | D | D | — | — |
| II-A isomer of Compound 21' | " | D | D | D | C | D | D | D | D | D | D | — | — |
| II-A isomer of Compound 22' | " | D | D | D | C | D | D | D | D | D | D | — | — |
| II-A isomer of Compound 23' | " | D | D | D | C | D | D | D | D | D | D | — | — |
| II-A isomer of Compound 24' | " | D | D | D | D | D | D | D | D | D | D | — | — |
| II-A isomer of Compound 25' | " | D | D | D | D | D | D | D | D | D | D | — | — |
| II-A isomer of Compound 26' | " | D | D | D | D | D | D | D | D | D | D | — | — |
| II-A isomer of Compound 27' | " | D | D | D | D | D | D | D | D | D | D | — | — |
| II-A isomer of Compound 28' | " | D | D | D | D | D | D | D | D | D | D | — | — |
| II-A isomer of Compound 29' | " | D | D | D | D | D | D | D | D | D | D | — | — |
| II-A isomer of Compound 30' | " | D | D | C | D | D | D | D | D | D | D | — | — |
| II-A isomer of Compound 31' | " | D | D | D | D | D | D | D | D | D | D | — | — |
| II-A isomer of Compound 32' | " | D | D | D | D | D | D | D | D | D | D | — | — |
| II-A isomer of Compound 33' | " | D | D | D | D | D | D | D | D | D | D | — | — |
| II-B isomer of Compound 1' | " | D | D | D | D | D | D | D | D | D | D | — | — |
| II-B isomer of Compound 2' | " | D | D | D | D | D | D | D | D | D | D | — | — |
| II-B isomer of Compound 3' | " | D | D | D | D | D | D | D | D | D | D | — | — |
| II-B isomer of Compound 4' | " | D | D | D | D | D | D | D | D | D | D | — | — |
| II-B isomer of Compound 5' | " | D | D | C | D | D | D | D | D | D | D | — | — |
| II-B isomer of Compound 6' | " | D | D | D | D | D | D | D | D | D | D | — | — |
| II-B isomer of Compound 7' | " | D | D | D | D | D | D | D | D | D | D | — | — |
| II-B isomer of Compound 8' | " | D | D | D | D | D | D | D | D | D | D | — | — |
| II-B isomer of Compound 9' | " | D | D | D | D | D | D | D | D | D | D | — | — |
| II-B isomer of Compound 10' | " | D | D | D | D | D | D | D | D | D | D | — | — |
| II-B isomer of Compound 11' | " | D | D | D | C | D | D | D | D | D | D | — | — |
| II-B isomer of Compound 12' | " | D | D | D | D | D | D | D | D | D | D | — | — |
| II-B isomer of Compound 13' | 20 | D | D | D | D | D | D | D | D | D | D | — | — |
| II-B isomer of Compound 14' | 5 | D | D | D | D | D | D | D | D | D | D | — | — |
| II-B isomer of Compound 15' | " | D | D | D | D | D | D | D | D | D | D | — | — |
| II-B isomer of Compound 16' | " | D | D | D | D | D | D | D | D | D | D | — | — |
| II-B isomer of Compound 17' | " | D | D | D | D | D | D | D | D | D | D | — | — |
| II-B isomer of Compound 18' | " | D | D | D | D | D | D | D | D | D | D | — | — |
| II-B isomer of Compound 19' | " | D | D | D | D | D | D | D | D | D | D | — | — |
| II-B isomer of Compound 20' | " | D | D | C | C | D | D | D | D | D | D | — | — |
| II-B isomer of Compound 21' | " | D | D | D | C | D | D | D | D | D | D | — | — |
| II-B isomer of | " | D | D | D | C | D | D | D | D | D | D | — | — |

TABLE 3-continued

| Test Compound No. | Concentration of active ingredient (ppm) | Degree of growth inhibition | | | | | | | | | | | |
|---|---|---|---|---|---|---|---|---|---|---|---|---|---|
| | | Hg | Pi | Vi | Vm | Mm | Dc | Un | Va | St | Cb | Fo | Ak |
| II-B isomer of Compound 22' | " | D | D | C | C | D | D | D | D | D | D | — | — |
| II-B isomer of Compound 23' | " | D | D | D | D | D | D | D | D | D | D | — | — |
| II-B isomer of Compound 24' | " | D | D | D | D | D | D | D | D | D | D | — | — |
| II-B isomer of Compound 25' | " | D | D | D | D | D | D | D | D | D | D | — | — |
| II-B isomer of Compound 26' | " | D | D | D | D | D | D | D | D | D | D | — | — |
| II-B isomer of Compound 27' | " | D | D | D | D | D | D | D | D | D | D | — | — |
| II-B isomer of Compound 28' | " | D | D | D | D | D | D | D | D | D | D | — | — |
| II-B isomer of Compound 29' | " | D | D | D | D | D | D | D | D | D | D | — | — |
| II-B isomer of Compound 30' | " | D | D | D | D | D | D | D | D | D | D | — | — |
| II-B isomer of Compound 31' | " | D | D | C | C | D | D | D | D | D | D | — | — |
| II-B isomer of Compound 32' | " | D | D | D | D | D | D | D | D | D | D | — | — |
| II-B isomer of Compound 33' | " | D | D | D | D | D | D | D | D | D | D | — | — |

TEST EXAMPLE 2

Protective Activity on Brown Leaf Spot of Peanut (*Cercospora arachidicola*)

Sandy loam was filled in a 150-ml plastic pot, and peanut (var.: Hanritsusei) was sowed at a rate of 1 seed/pot and cultivated for 12 days in an air-conditioned greenhouse (25° to 30° C.) to obtain young seedlings in a third true leaf stage. At that time, the aqueous dilute liquor of the emulsifiable concentrate of each test compound was sprayed on the foliage at a rate of 10 ml/pot. After air-drying, the young seedlings were inoculated with *Cercospora arachidicola*, covered with a polyvinyl chloride film for keeping humidity and placed in an air-conditioned greenhouse kept at 25° to 30° C. The seedlings were cultivated for further additional 10 days in the greenhouse in order to sufficiently infect them, and the appearance for signs of disease of the leaves was observed. The disease severity was calculated as follows: The leaves were measured for a percentage of infected area and classified into the corresponding disease indices, 0, 0.5, 1, 2, 4; and the disease severity was calculated according to the following equation.

| Disease index | Disease appearance |
|---|---|
| 0 | No colony nor infected area on leaf surface |
| 0.5 | Colony or infected area of less than 5% on leaf surface |
| 1 | Colony or infected area of less than 20% on leaf surface |
| 2 | Colony or infected area of less than 50% on leaf surface |
| 4 | Colony or infected area of not less than 50% on leaf surface |

Disease severity (%) = $\frac{\Sigma(\text{Disease index}) \times (\text{number of leaves})}{4 \times (\text{Total number of leaves examined})} \times 100$ The control of disease was then calculated according to the following equation.

Control of disease (%) = $100 - \frac{(\text{Disease severity in treated plot})}{(\text{Disease severity in untreated plot})} \times 100$ As a result, it was found from Table 4 that the I-A isomer of the compounds of the present invention has a remarkably high protective activity as compared with its I-B isomer.

TABLE 4

| Compound No. | Kind of geometrical iosmer | Concentration of active ingredient (ppm) | Control of disease (%) |
|---|---|---|---|
| Test compound | | | |
| 1 | I-A isomer | 250 | 100 |
| 2 | " | " | " |
| 3 | " | " | " |
| 4 | " | " | " |
| 5 | " | " | " |
| 9 | " | " | " |
| 20 | " | " | " |
| 21 | " | " | " |
| 23 | " | " | " |
| 26 | " | " | " |
| 27 | " | " | " |
| 29 | " | " | " |
| 30 | " | " | " |
| 31 | " | " | " |
| 32 | " | " | " |
| 33 | " | " | " |
| 34 | " | " | " |
| (Reference compound) | | | |
| 1 | I-B isomer | 250 | 0 |
| 2 | " | " | " |
| 3 | " | " | " |
| 4 | " | " | " |
| 5 | " | " | " |
| 9 | " | " | " |
| 20 | " | " | " |
| 21 | " | " | " |
| 23 | " | " | " |
| 26 | " | " | " |
| 27 | " | " | " |
| 29 | " | " | " |
| 30 | " | " | " |
| 31 | " | " | " |
| 32 | " | " | " |

TABLE 4-continued

| Compound No. | Kind of geometrical iosmer | Concentration of active ingredient (ppm) | Control of disease (%) |
|---|---|---|---|
| 33 | " | " | " |
| 34 | " | " | " |
| Commercial fungicide (Cl,CN,Cl,Cl,Cl,CN benzene) | | " | 100 |

TEST EXAMPLE 3

Protective Activity of Gray Mold of Cucumber (*Botrytis cinerea*)

Sandy loam was filled in a 150-ml plastic pot, and cucumber (var.: Sagami-hanjiro) was sowed at a rate of 3 seed/pot and cultivated for 8 days in a greenhouse to obtain young seedlings in a cotyledonous stage. At that time, the aqueous dilute liquor of the emulsifiable concentrate of each test compound was sprayed on the foliage at a rate of 10 ml/pot. After air-drying, the young seedlings were inoculated with *Botrytis cinerea* and placed in a humid, constant temperature chamber kept at 20° C. After 3 days, the disease appearance of the cotyledon was observed. The examination of infection and calculation of the control of disease were carried out in the same manner as in Test Example 2.

As a result, it was found from Table 5 that the I-A isomer of Compound 1 has a remarkably high protective activity as compared with its I-B isomer.

TABLE 5

| Compound | Concentration of active ingredient (ppm) | Control of disease (%) |
|---|---|---|
| I-A isomer of Compound 1 | 500 | 100 |
| I-B isomer of Compound 1 | " | 10 |
| (1) benzimidazole-CONHC4H9, NHCOOCH3 | " | 90 |

Note:
(1) Commercial fungicide

TEST EXAMPLE 4

Protective Activity on Leaf Rust of Wheat (*Puccinia recondita*) (curative effect) (young seedling test)

Sandy loam was filled in a 150-ml plastic pot, and wheat (var.: Norin No. 61) was sowed at a rate of 10 to 15 seed/pot and cultivated for 7 days in an air-conditioned greenhouse (18° to 23° C.) to obtain young seedlings in a first true leaf stage. The seedlings were then inoculated with *Puccinia recondita* and infected by placing them for 16 hours in a humid chamber kept at 23° C. At that time, the aqueous dilute liquor of the emulsifiable concentrate of each test compound was sprayed thereon at a rate of 10 ml/pot. The seedlings were cultivated for 10 days in a constant temperature room (23° C.) under a fluorescent light, and then the disease appearance of the first true leaf was observed. The examination of infection and calculation of the control of disease were carried out in the same manner as in Test Example 2.

As a result, it was found from Table 6 that the I-A isomer of the present compounds had a clearly high protective activity as compared with not only its I-B isomer but also the commercial fungicide and the well-known compound.

TABLE 6

| Test Compound | | Control of disease (%) Concentration of active ingredient | | |
|---|---|---|---|---|
| Compound No. | Kind of geometrical isomer | 100 ppm | 20 ppm | 5 ppm |
| 1 | I-A | 100 | 100 | 100 |
|  | I-B | 100 | 95 | 25 |
| 2 | I-A | 100 | 100 | 100 |
|  | I-B | 100 | 93 | 21 |
| 3 | I-A | 100 | 100 | 100 |
|  | I-B | 100 | 95 | 30 |
| 4 | I-A | 100 | 99 | 86 |
|  | I-B | 100 | 64 | 0 |
| 9 | I-A | 100 | 85 | 27 |
|  | I-B | 94 | 60 | 0 |
| 17 | I-A | 100 | 87 | 36 |
|  | I-B | 72 | 63 | 0 |
| 21 | I-A | 100 | 89 | 15 |
|  | I-B | 78 | 56 | 0 |
| 26 | I-A | 100 | 100 | 100 |
|  | I-B | 100 | 60 | 0 |
| 27 | I-A | 100 | 100 | 100 |
|  | I-B | 100 | 95 | 20 |
| 29 | I-A | 100 | 100 | 100 |
|  | I-B | 100 | 75 | 0 |
| 30 | I-A | 100 | 100 | 100 |
|  | I-B | 100 | 0 | 0 |
| 31 | I-A | 100 | 100 | 100 |
|  | I-B | 100 | 55 | 0 |
| 32 | I-A | 100 | 100 | 100 |
|  | I-B | 100 | 64 | 0 |
| 33 | I-A | 100 | 100 | 100 |
|  | I-B | 100 | 32 | 0 |
| 34 | I-A | 100 | 90 | 36 |
|  | I-B | 100 | 0 | 0 |
| 36 | I-A | 100 | 100 | 96 |
|  | I-B | 100 | 73 | 0 |
| 39 | I-A | 100 | 100 | 30 |
|  | I-B | 93 | 63 | 0 |
| Well-known compound as a reference | | 56 | 50 | 0 |

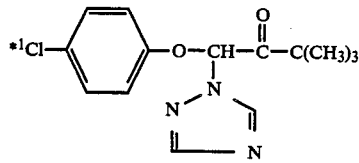

*1 | | 64 | 53 | 0

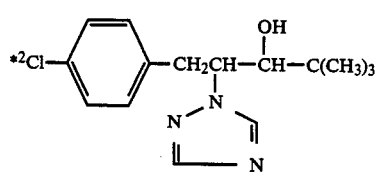

*2

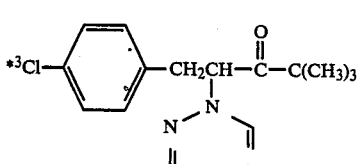

*3 | | 58 | 58 | 0

TABLE 6-continued

| Test Compound | | Control of disease (%) Concentration of active ingredient | | |
|---|---|---|---|---|
| Compound No. | Kind of geometrical isomer | 100 ppm | 20 ppm | 5 ppm |
| *4 (PhCH₂CH(N-triazole)-C(O)-Ph) | | 50 | 14 | 0 |
| *5 (PhCH₂CH(N-triazole)-CH(OH)-Ph) | | 0 | 0 | 0 |
| *6 (4-Cl-C₆H₄-CH=C(N-triazole)-C(O)-Ph) | | 100 | 0 | 0 |
| *7 (triazole-N-CH₂C(O)-C(CH₃)₃) | | 0 | 0 | 0 |

Note:
*¹Commercial fungicide, a compound disclosed in B.P. No. 1364619.
*²Compound disclosed in West German Patent No. 2734426.
*³Compound disclosed in Belgian Patent No. 845433.
*⁴Compound disclosed in West German Patent No. 2610022.
*⁵Compound disclosed in West German Patent No. 2654890.
*⁶Compound disclosed in U.S. Pat. No. 4086351.
*⁷Compound disclosed in B.P. No. 1464224.

TEST EXAMPLE 5

Protective Activity on Stem Rust of Wheat (*Puccinia graminis*) (curative effect) (young seedling test)

Young seedlings of wheat (var.: Norin No. 61) were obtained in the same manner as in Test Example 4. The seedlings were then inoculated with *Puccinia graminis* and infected by placing them for 16 hours in a humid chamber kept at 23° C. At that time, the aqueous dilute liquor of the emulsifiable concentrate of each test compound was sprayed thereon at a rate of 10 ml/pot. The seedlings were cultivated for 10 days in an air-conditioned greenhouse kept at 23° C., and then the disease appearance of the first true leaf was observed. The examination of infection and calculation of the control of disease were carried out in the same manner as in Test Example 2.

As a result, it was found from Table 7 that the I-A isomer of the present compounds has a clearly high protective activtiy as compared with not only its I-B isomer but also the commercial fungicide and the well-known compound.

TABLE 7

| Test compound | | Concentration of active ingredient (ppm) | Control of disease (%) |
|---|---|---|---|
| Compound No. | Kind of geometrical isomer | | |
| 1 | I-A | 100 | 100 |
| | | 20 | 100 |
| | | 5 | 1000 |
| | I-B | 100 | 100 |
| | | 20 | 95 |
| | | 5 | 25 |
| 2 | I-A | 100 | 100 |
| | | 20 | 100 |
| | | 5 | 100 |
| | I-B | 100 | 100 |
| | | 20 | 93 |
| | | 5 | 21 |
| 3 | I-A | 100 | 100 |
| | | 20 | 100 |
| | | 5 | 100 |
| | I-B | 100 | 100 |
| | | 20 | 95 |
| | | 5 | 30 |
| 20 | I-A | 100 | 100 |
| | | 20 | 100 |
| | | 5 | 100 |
| | I-B | 50 | 0 |
| 26 | I-A | 100 | 100 |
| | | 20 | 100 |
| | | 5 | 100 |
| | I-B | 50 | 0 |
| 27 | I-A | 100 | 100 |
| | | 20 | 100 |
| | | 5 | 100 |
| | I-B | 100 | 100 |
| | | 20 | 90 |
| | | 5 | 30 |
| 30 | I-A | 100 | 100 |
| | | 20 | 100 |
| | | 5 | 100 |
| | I-B | 50 | 80 |
| 31 | I-A | 100 | 100 |
| | | 20 | 100 |
| | | 5 | 100 |
| | I-B | 50 | 0 |
| 32 | I-A | 100 | 100 |
| | | 20 | 100 |
| | | 5 | 100 |
| | I-B | 50 | 0 |

Well-known compound as a reference

| Compound | Conc. (ppm) | Control (%) |
|---|---|---|
| 4-Cl-C₆H₄-O-CH(N-triazole)-C(O)-C(CH₃)₃  *1 | 100 | 84 |
| | 20 | 13 |
| | 5 | 0 |
| 4-Cl-C₆H₄-CH₂CH(N-triazole)-CH-C(O)-C(CH₃)₃  *2 | 100 | 87 |
| | 20 | 18 |
| | 5 | 0 |

TABLE 7-continued

| Test compound | | Concentration of active ingredient (ppm) | Control of disease (%) |
|---|---|---|---|
| Compound No. | Kind of geometrical isomer | | |
| 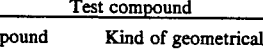 *3 | | 50 | 0 |

Note:
*1 Commercial fungicide, a compound disclosed in B.P. No. 1364619.
*2 Compound disclosed in West German Patent No. 2734426.
*3 Compound disclosed in U.S. Pat. No. 4086351.

TEST EXAMPLE 6

Protective Activity on Powdery Mildew of Barley (*Erysiphe graminis*) by foliar application (young seedling test)

Sandy loam was filled in a 150-ml plastic pot, and barley (var.: Goseshikoku) was sowed at a rate of 10–15 seed/pot and cultivated for 7 days in an air-conditioned greenhouse (18° to 23° C.) to obtain young seedlings in a first true leaf stage. Thereafter, the aqueous dilute liquor of the emulsifiable concentrate of each test compound was sprayed on the foliage at a rate of 10 ml/pot. After air-drying, the young seedlings were inoculated with *Erysiphe graminis* and cultivated for 10 days in a constant temperature room (23° C.) under a fluorescent light. The disease appearance of the first true leaf was then observed. The disease severity was calculated as follows: The leaves were measured for a percentage of infected area and classified into the corresponding disease indices, 0, 0.5, 1, 2, 4; and the disease severity was calculated according to the following equation.

| Disease index | Disease appearance |
|---|---|
| 0 | No colony on leaf surface |
| 0.5 | Colony of less than 5% on leaf surface |
| 1 | Colony of less than 20% on leaf surface |
| 2 | Colony of less than 50% on leaf surface |
| 4 | Colony of not less than 50% on leaf surface |

$$\text{Disease severity (\%)} = \frac{\Sigma(\text{Disease index}) \times (\text{number of leaves})}{4 \times (\text{Total number of leaves examined})} \times 100$$

The control of disease was then calculated according to the following equation.

$$\text{Control of disease (\%)} = 100 - \frac{(\text{Disease severity in treated plot})}{(\text{Disease severity in untreated plot})} \times 100$$

As a result, it was found from Table 8 that the present compounds have an excellent protective activity against powdery mildew of barley, and that the activitiy is equal or superior to that of the reference compound.

TABLE 8

| Test compound | | Concentration of active ingredient (ppm) | Control of disease (%) |
|---|---|---|---|
| Compound No. | Kind of geometrical isomer | | |
| 1 | I-A isomer | 500 | 100 |
| 2 | " | " | " |
| 3 | " | " | " |
| 4 | " | " | " |
| 5 | " | " | " |
| 6 | " | " | " |
| 7 | " | " | " |
| 8 | " | " | " |
| 9 | " | " | " |
| 10 | " | " | " |
| 11 | " | " | " |
| 12 | " | " | " |
| 13 | " | " | " |
| 14 | " | " | " |
| 15 | " | " | " |
| 16 | " | " | " |
| 17 | " | " | " |
| 18 | " | " | " |
| 19 | " | " | " |
| 20 | " | " | " |
| 21 | " | " | " |
| 22 | " | " | " |
| 23 | " | " | " |
| 24 | " | " | " |
| 25 | " | " | " |
| 26 | " | " | " |
| 27 | " | " | " |
| 28 | " | " | " |
| 29 | " | " | " |
| 30 | " | 200 | " |
| 31 | " | " | " |
| 32 | " | " | " |
| 33 | " | " | " |
| 34 | " | " | " |
| 35 | " | 50 | " |
| 36 | " | " | " |
| 37 | " | " | " |
| 38 | " | " | " |
| 39 | " | " | " |
| 40 | " | " | 90 |
| 41 | " | " | 91 |
| 42 | " | " | 89 |
| 43 | " | " | 93 |
| 44 | " | " | 100 |
| 45 | " | " | " |
| 46 | " | " | 95 |
| 47 | " | " | 100 |
| 48 | " | " | 95 |
| 49 | " | " | 100 |
| 50 | " | " | 80 |
| 51 | " | " | 100 |
| 52 | " | " | " |
| 1 | I-B isomer | 500 | " |
| 2 | " | " | " |
| 3 | " | " | " |
| 4 | " | " | " |
| 5 | " | " | " |
| 6 | " | " | " |
| 7 | " | " | " |
| 8 | " | " | " |
| 9 | " | " | " |
| 10 | " | " | " |
| 11 | " | " | " |
| 13 | " | " | " |
| 14 | " | " | " |
| 15 | " | " | " |
| 16 | " | " | " |
| 17 | " | " | " |
| 18 | " | " | " |
| 19 | " | " | " |
| 20 | " | " | " |
| 21 | " | " | " |
| 22 | " | " | " |
| 23 | " | " | " |
| 24 | " | " | " |
| 25 | " | " | " |

TABLE 8-continued

| Test compound | | Concentration of active ingredient (ppm) | Control of disease (%) |
|---|---|---|---|
| Compound No. | Kind of geometrical isomer | | |
| 26 | " | " | " |
| 27 | " | " | " |
| 28 | " | " | " |
| 29 | " | " | " |
| 30 | " | " | " |
| 31 | " | " | " |
| 32 | " | " | " |
| 33 | " | " | " |
| 34 | " | " | " |
| 35 | " | " | " |
| 36 | " | " | " |
| 38 | " | " | " |
| 39 | " | " | " |
| 43 | " | " | " |
| 47 | " | " | " |
| 51 | " | " | " |
| 1' | II-A isomer | " | " |
| 2' | " | " | " |
| 3' | " | " | " |
| 4' | " | " | " |
| 5' | " | " | " |
| 6' | " | " | " |
| 7' | " | " | " |
| 8' | " | " | " |
| 9' | " | " | " |
| 10' | " | " | " |
| 11' | " | " | " |
| 12' | " | " | " |
| 13' | " | " | " |
| 14' | " | " | " |
| 15' | " | " | " |
| 16' | " | " | " |
| 17' | " | " | " |
| 18' | " | " | " |
| 19' | " | " | " |
| 20' | " | " | " |
| 21' | " | " | " |
| 22' | " | " | " |
| 23' | " | " | " |
| 24' | " | " | " |
| 25' | " | " | " |
| 26' | " | " | " |
| 27' | " | " | " |
| 28' | " | " | " |
| 29' | " | " | " |
| 30' | " | " | " |
| 31' | " | " | " |
| 32' | " | " | " |
| 33' | " | " | " |
| 1' | II-B isomer | " | " |
| 2' | " | " | " |
| 3' | " | " | " |
| 4' | " | " | " |
| 5' | " | " | " |
| 6' | " | " | " |
| 7' | " | " | " |
| 8' | " | " | " |
| 9' | " | " | " |
| 10' | " | " | " |
| 11' | " | " | " |
| 12' | " | " | " |
| 13' | " | " | " |
| 14' | " | " | " |
| 15' | " | " | " |
| 16' | " | " | " |
| 17' | " | " | " |
| 18' | " | " | " |
| 19' | " | " | " |
| 20' | " | " | " |
| 21' | " | " | " |
| 22' | " | " | " |
| 23' | " | " | " |
| 24' | " | " | " |
| 25' | " | " | " |
| 26' | " | " | " |
| 27' | " | " | " |
| 28' | " | " | " |
| 29' | " | " | " |
| 30' | " | " | " |
| 31' | " | " | " |
| 32' | " | " | " |
| 33' | " | " | " |
| Reference compound | | 500 | 100 |
| (Commercial fungicide, 2,6-dimethyl-morpholine with $N-C_{13}H_{27}$) | | 200 | 81 |
| | | 50 | 43 |

TEST EXAMPLE 7

Five hundred grams of soil mixture comprising sea sand, mountain soil and peat wer placed in a flower pot of 13 cm in diameter, and Pot-mum (var.: Snow Ridge) was cultivated therein. Two weeks after setting, the Pot-mum was pinched and cultivated in a 3-stem form, and then new buds grew. Two weeks after pinching, an aqueous dilute liquor containing a pre-determined concentration of each test compound was applied to the Pot-mum, and 42 days after the application of pesticide, the plant growth controlling effect was examined. The results are shown in Table 9.

The effect was evaluated as follows: An increase in plant height was calculated as a difference between the initial plant height at the time of the application and the plant height on the 42nd day after the application, and expressed in height index with the corresponding difference in the untreated plot as 100. The values in the table are a mean value of three replications.

As a reference compound, B-Nine (N,N-dimethylaminosuccinamic acid) was used.

TABLE 9

Dwarfing test for Pot-mum

| Compound | Comcentration of active ingredient (ppm) | Height (%) | Maximum leaf length (%) | Flower diameter (%) | Phytotoxicity |
|---|---|---|---|---|---|
| I-A isomer of Compound 1 | 500 | 65 | 97 | 98 | None |
| I-B isomer of Compound 1 | 500 | 81 | 102 | 105 | None |
| I-A isomer of Compound 4 | 500 | 73 | 100 | 101 | None |
| I-B isomer of Compound 4 | 500 | 85 | 101 | 102 | None |
| I-A isomer of Compound 9 | 500 | 67 | 99 | 98 | None |
| I-B isomer of Compound 9 | 500 | 88 | 100 | 100 | None |
| I-A isomer of Compound 11 | 500 | 57 | 95 | 95 | None |
| I-B isomer of Compound 11 | 500 | 81 | 102 | 100 | None |
| I-A isomer of Compound 21 | 500 | 73 | 97 | 99 | None |
| I-B isomer of Compound 21 | 500 | 86 | 97 | 101 | None |
| I-A isomer of | 500 | 75 | 101 | 100 | None |

TABLE 9-continued

Dwarfing test for Pot-mum

| Compound | Concentration of active ingredient (ppm) | Height (%) | Maximum leaf length (%) | Flower diameter (%) | Phytotoxicity |
|---|---|---|---|---|---|
| Compound 26 | | | | | |
| I-B isomer of Compound 26 | 500 | 88 | 100 | 98 | None |
| I-A isomer of Compound 30 | 1000 | 63 | — | — | None |
| I-A isomer of Compound 31 | 1000 | 65 | — | — | None |
| I-A isomer of Compound 35 | 500 | 64 | 101 | 98 | None |
| I-A isomer of Compound 43 | 500 | 62 | 98 | 100 | None |
| I-B isomer of Compound 35 | 500 | 89 | 102 | 101 | None |
| B-Nine *1 | 4000 | 86 | 98 | 103 | None |
| No treatment | — | 100 | 100 | 100 | None |

*1 Reference compound (commercial fungicide)

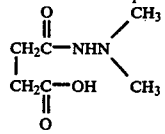

TEST EXAMPLE 8

Herbicidal Activity Test on Field Weeds

Soil was mixed with the seeds of large crabgrass (*Digitaria sanguinalis*), redroot pigweed (*Amaranthus retroflexus*) and common lambsquarter (*Chenopodium album*) and filled in a 1/5000 are Wagner's pot. Thereafter, the aqueous dilute liquor of the emulsifiable concentrate containing a pre-determined amount of active ingredient was applied to the surface of the soil by means of a hand sprayer. After the application, sugar beet seedlings (var.: Monohil) at a 5-leaf stage cultivated in paper pots were transplanted to the Wagner's pot. Thereafter, the seedlings were cultivated in a greenhouse. Twenty days after the application, the herbicidal activity and phytotoxicity to crops were observed. The results are shown in Table 10. The herbicidal activity was expressed by numerals, 0 to 5, as shown below, provided that the phytotoxicity to crops was also expressed on the same standard.

| 0 | Inhibition percentage | 0–9% |
| 1 | Inhibition percentage | 10–29% |
| 2 | Inhibition percentage | 30–49% |
| 3 | Inhibition percentage | 50–69% |
| 4 | Inhibition percentage | 70–89% |
| 5 | Inhibition percentage | 90–100% |

As apparent from Table 10, the I-A isomer of the present compounds showed a far strong herbicidal activity as compared with the I-B isomer.

TABLE 10

| Compound | Dosage (g/a) | Herbicidal activity Large crabgrass | Redroot pigweed | Common lambsquarter | Phytotoxicity to sugar beet |
|---|---|---|---|---|---|
| I-A isomer of Compound 1 | 40 | 5 | 5 | 5 | 0 |
| | 20 | 4 | 5 | 5 | 0 |
| I-B isomer of Compound 1 | 40 | 3 | 4 | 4 | 0 |
| | 20 | 2 | 3 | 3 | 0 |
| I-A isomer of Compound 2 | 40 | 4 | 5 | 5 | 0 |
| | 20 | 4 | 4 | 5 | 0 |
| I-B isomer of Compound 2 | 40 | 3 | 3 | 3 | 0 |
| | 20 | 1 | 3 | 3 | 0 |
| I-A isomer of Compound 3 | 40 | 5 | 5 | 5 | 0 |
| | 20 | 4 | 5 | 5 | 0 |
| I-B isomer of Compound 3 | 40 | 3 | 3 | 3 | 0 |
| | 20 | 2 | 3 | 3 | 0 |
| I-A isomer of Compound 4 | 40 | 5 | 5 | 5 | 0 |
| | 20 | 4 | 5 | 5 | 0 |
| I-B isomer of Compound 4 | 40 | 3 | 3 | 3 | 0 |
| | 20 | 1 | 2 | 3 | 0 |
| I-A isomer of Compound 5 | 40 | 4 | 5 | 5 | 0 |
| | 20 | 4 | 4 | 5 | 0 |
| I-B isomer of Compound 5 | 40 | 2 | 2 | 3 | 0 |
| | 20 | 2 | 2 | 1 | 0 |
| I-A isomer of Compound 6 | 160 | 4 | 5 | 5 | 0 |
| | 80 | 4 | 5 | 5 | 0 |
| I-B isomer of Compound 6 | 160 | 2 | 3 | 2 | 0 |
| | 80 | 1 | 1 | 2 | 0 |
| I-A isomer of Compound 7 | 40 | 5 | 5 | 5 | 0 |
| | 20 | 4 | 4 | 5 | 0 |
| I-B isomer of Compound 7 | 40 | 3 | 3 | 3 | 0 |
| | 20 | 2 | 3 | 3 | 0 |
| I-A isomer of Compound 8 | 40 | 4 | 5 | 5 | 0 |
| | 20 | 4 | 4 | 4 | 0 |
| I-B isomer of Compound 8 | 40 | 2 | 3 | 4 | 0 |
| | 20 | 1 | 2 | 3 | 0 |
| I-A isomer of Compound 9 | 40 | 5 | 5 | 5 | 0 |
| | 20 | 4 | 5 | 5 | 0 |
| I-B isomer of Compound 9 | 40 | 2 | 3 | 3 | 0 |
| | 20 | 2 | 1 | 3 | 0 |
| I-A isomer of Compound 10 | 40 | 5 | 4 | 5 | 0 |
| | 20 | 4 | 4 | 4 | 0 |
| I-B isomer of Compound 10 | 40 | 2 | 3 | 3 | 0 |
| | 20 | 2 | 2 | 3 | 0 |
| I-A isomer of Compound 11 | 40 | 5 | 5 | 5 | 0 |
| | 20 | 4 | 5 | 5 | 0 |
| I-B isomer of Compound 11 | 40 | 3 | 4 | 4 | 0 |
| | 20 | 3 | 2 | 2 | 0 |
| I-A isomer of Compound 12 | 160 | 4 | 4 | 4 | 0 |
| | 80 | 4 | 4 | 4 | 0 |
| I-A isomer of Compound 13 | 160 | 4 | 5 | 5 | 0 |
| | 80 | 4 | 4 | 5 | 0 |
| I-B isomer of Compound 13 | 160 | 2 | 4 | 3 | 0 |
| | 80 | 1 | 1 | 2 | 0 |
| I-A isomer of Compound 14 | 80 | 4 | 5 | 5 | 0 |
| | 40 | 4 | 5 | 5 | 0 |
| I-B isomer of Compound 14 | 80 | 3 | 4 | 3 | 0 |
| | 40 | 2 | 3 | 3 | 0 |
| I-A isomer of Compound 15 | 40 | 5 | 5 | 5 | 0 |
| | 20 | 4 | 4 | 4 | 0 |
| I-B isomer of Compound 15 | 40 | 3 | 4 | 3 | 0 |
| | 20 | 3 | 3 | 2 | 0 |
| I-A isomer of Compound 16 | 80 | 5 | 5 | 5 | 0 |
| | 40 | 4 | 5 | 5 | 0 |
| I-B isomer of Compound 16 | 80 | 1 | 3 | 3 | 0 |
| | 40 | 0 | 3 | 3 | 0 |
| I-A isomer of Compound 17 | 40 | 5 | 5 | 5 | 0 |
| | 20 | 4 | 4 | 5 | 0 |
| I-B isomer of Compound 17 | 40 | 1 | 2 | 2 | 0 |
| | 20 | 0 | 1 | 2 | 0 |
| I-A isomer of Compound 18 | 80 | 4 | 5 | 4 | 0 |
| | 40 | 4 | 4 | 4 | 0 |
| I-B isomer of Compound 18 | 80 | 0 | 1 | 2 | 0 |
| | 40 | 0 | 1 | 1 | 0 |
| I-A isomer of Compound 19 | 80 | 5 | 5 | 5 | 0 |
| | 40 | 4 | 5 | 5 | 0 |
| I-B isomer of Compound 19 | 80 | 3 | 3 | 3 | 0 |
| | 40 | 2 | 1 | 3 | 0 |
| I-A isomer of Compound 20 | 160 | 4 | 5 | 5 | 0 |
| | 80 | 4 | 4 | 4 | 0 |
| I-B isomer of Compound 20 | 160 | 2 | 4 | 3 | 0 |
| | 80 | 0 | 2 | 1 | 0 |
| I-A isomer of Compound 21 | 160 | 5 | 5 | 5 | 0 |
| | 80 | 4 | 5 | 5 | 0 |
| I-B isomer of Compound 21 | 160 | 3 | 3 | 2 | 0 |
| | 80 | 2 | 1 | 2 | 0 |

TABLE 10-continued

| Compound | Dosage (g/a) | Large crab-grass | Redroot pigweed | Common lambs-quarter | Phyto-toxicity to sugar beet |
|---|---|---|---|---|---|
| I-A isomer of Compound 22 | 160 | 4 | 4 | 4 | 0 |
|  | 80 | 4 | 4 | 4 | 0 |
| I-B isomer of Compound 22 | 160 | 2 | 4 | 3 | 0 |
|  | 80 | 1 | 1 | 2 | 0 |
| I-A isomer of Compound 23 | 80 | 4 | 5 | 5 | 0 |
|  | 40 | 4 | 5 | 5 | 0 |
| I-B isomer of Compound 23 | 80 | 2 | 2 | 2 | 0 |
|  | 40 | 0 | 1 | 2 | 0 |
| I-A isomer of Compound 24 | 80 | 4 | 4 | 5 | 0 |
|  | 40 | 4 | 4 | 4 | 0 |
| I-A isomer of Compound 25 | 160 | 5 | 5 | 5 | 0 |
|  | 80 | 4 | 5 | 4 | 0 |
| I-B isomer of Compound 25 | 160 | 2 | 4 | 3 | 0 |
|  | 80 | 0 | 2 | 3 | 0 |
| I-A isomer of Compound 26 | 40 | 5 | 5 | 5 | 0 |
|  | 20 | 4 | 5 | 5 | 0 |
| I-A isomer of Compound 27 | 40 | 5 | 5 | 5 | 0 |
|  | 20 | 4 | 5 | 5 | 0 |
| I-A isomer of Compound 35 | 40 | 5 | 5 | 5 | 0 |
|  | 20 | 5 | 5 | 5 | 0 |
| I-A isomer of Compound 36 | 80 | 5 | 5 | 5 | 0 |
|  | 40 | 4 | 4 | 5 | 0 |
| I-A isomer of Compound 37 | 160 | 5 | 5 | 5 | 0 |
|  | 80 | 4 | 5 | 5 | 0 |
| I-A isomer of Compound 38 | 80 | 5 | 5 | 5 | 0 |
|  | 40 | 4 | 4 | 4 | 0 |
| I-A isomer of Compound 39 | 80 | 4 | 5 | 5 | 0 |
|  | 40 | 4 | 5 | 5 | 0 |
| I-A isomer of Compound 40 | 40 | 5 | 5 | 5 | 0 |
|  | 20 | 4 | 5 | 4 | 0 |
| I-A isomer of Compound 41 | 80 | 5 | 5 | 5 | 0 |
|  | 40 | 5 | 4 | 4 | 0 |
| I-A isomer of Compound 42 | 40 | 4 | 5 | 5 | 0 |
|  | 20 | 4 | 4 | 5 | 0 |
| I-A isomer of Compound 43 | 80 | 5 | 5 | 5 | 0 |
|  | 40 | 5 | 5 | 5 | 0 |
| I-A isomer of Compound 44 | 80 | 5 | 5 | 5 | 0 |
|  | 40 | 4 | 5 | 5 | 0 |
| I-A isomer of Compound 45 | 160 | 5 | 5 | 5 | 0 |
|  | 80 | 4 | 5 | 5 | 0 |
| I-A isomer of Compound 46 | 160 | 4 | 5 | 5 | 0 |
|  | 80 | 4 | 5 | 4 | 0 |
| I-A isomer of Compound 47 | 80 | 5 | 5 | 5 | 0 |
|  | 40 | 5 | 5 | 5 | 0 |
| I-A isomer of Compound 48 | 160 | 4 | 5 | 5 | 0 |
|  | 80 | 4 | 5 | 5 | 0 |
| I-A isomer of Compound 49 | 160 | 4 | 5 | 4 | 0 |
|  | 80 | 4 | 4 | 4 | 0 |
| I-A isomer of Compound 50 | 80 | 5 | 5 | 5 | 0 |
|  | 40 | 4 | 5 | 5 | 0 |
| I-B isomer of Compound 35 | 40 | 2 | 3 | 3 | 0 |
|  | 20 | 1 | 2 | 2 | 0 |
| I-B isomer of Compound 43 | 80 | 3 | 3 | 3 | 0 |
|  | 40 | 2 | 3 | 1 | 0 |

TEST EXAMPLE 9

Height-Controlling Effect on Soybean and Barley

A 500-ml plastic pot was filled with sandy loam. The soil in the upper half of the pot was taken out, and mixed well with 10 ml of the aqueous dilute liquor of the emulsifiable concentrate of each test compound and returned to the pot. Thereafter, soybean and barley were sowed in the treated soil at rates of 3 seeds/pot and 5 seeds/pot, respectively.

The soybean and barley were cultivated in a glass house kept at 25° C., and after 14 days, the height of each plant was measured. The reslts are shown in Table 11. the numerical values in the table mean the average height of two soybeans and that of three barleys which were expressed in percentage with the corresponding average height in the untreated plot at 100.

As a result, it was found that the I-A isomer of the present compounds displayed a remarkably strong height-controlling effect as compared with the I-B isomer which is a reference compound. Further, with any of the I-A and the I-B isomers, no phytotoxicity such as chlorosis and necrosis was observed, and it was found that the leaves became rather deep green.

TABLE 11

| Test compound | Dosage rate (g/a) | Soybean (%) | Barley (%) |
|---|---|---|---|
| I-A isomer of Compound 1 | 10 | 18 | 17 |
|  | 5 | 22 | 18 |
|  | 2.5 | 37 | 26 |
| I-B isomer of Compound 1 | 10 | 22 | 52 |
|  | 5 | 28 | 47 |
|  | 2.5 | 46 | 89 |
| I-A isomer of Compound 35 | 10 | 20 | 70 |
|  | 5 | 33 | 88 |
|  | 2.5 | 54 | 95 |
| I-A isomer of Compound 40 | 10 | 21 | 57 |
|  | 5 | 28 | 78 |
|  | 2.5 | 47 | 102 |
| I-A isomer of Compound 43 | 10 | 19 | 76 |
|  | 5 | 24 | 100 |
|  | 2.5 | 50 | 102 |
| I-A isomer of Compound 47 | 10 | 33 | 89 |
|  | 5 | 45 | 98 |
|  | 2.5 | 72 | 97 |
| I-A isomer of Compound 50 | 10 | 44 | 77 |
|  | 5 | 65 | 89 |
|  | 2.5 | 97 | 98 |
| I-B isomer of Compound 35 | 10 | 85 | 98 |
|  | 5 | 93 | 102 |
|  | 2.5 | 99 | 100 |

TEST EXAMPLE 10

Controlling Effect on the Growth of Intercode of Barley

Barley (var.: Goseshikoku) was sowed in a field on November 20th, and the next year the aqueous dilute liquor of the emulsifiable concentrate of the I-A isomer of Compound 1 was sprayed on the foliage once (on April 4th) and twice (on April 4th and 24th).

The barley in each plot was reaped on May 28th, and the length of the internodes of 30 barley straws per plot was measured. As shown in Table 12, the length of, chiefly, the fourth and fifth internodes in the treated plot was outstandingly shortened as compared with the untreated plot, and the total length of the straw in the treated plot was also shortened.

Phytotoxicity such as yellowing and sterility were not observed.

TABLE 12

| Test compound | Treatment | 1st internode (cm) | 2nd (cm) | 3rd (cm) | 4th (cm) | 5th (cm) | 6th (cm) | 7th (cm) | Total length (cm) |
|---|---|---|---|---|---|---|---|---|---|
| No treatment | — | 32.1 | 17.5 | 15.7 | 13.7 | 11.4 | 9.5 | 6.5 | 106.4 |
| I-A isomer of Compound 1 | 25 ppm twice | 35.0 | 19.1 | 14.7 | 12.0 | 9.2 | 8.7 | 5.7 | 104.4 |
| I-A isomer of Compound 1 | 50 ppm once | 36.2 | 20.7 | 15.0 | 10.0 | 6.6 | 6.3 | 5.4 | 100.2 |

TABLE 12-continued

| Test compound | Treatment | 1st internode (cm) | 2nd (cm) | 3rd (cm) | 4th (cm) | 5th (cm) | 6th (cm) | 7th (cm) | Total length (cm) |
|---|---|---|---|---|---|---|---|---|---|
| I-A isomer of Compound 1 | 50 ppm twice | 36.8 | 19.1 | 12.8 | 9.2 | 7.4 | 7.1 | 6.1 | 98.5 |

TEST EXAMPLE 11

Growth Controlling Effect on Turf

Soil mixture, a 3:1 mixture of mountain soil and peat, was filled in a 1/5,000 are Wagner's pot, and Korai lawn grass (*Zoysia matrella* L) was transplanted thereto on December 6th.

The lawn grass was cultivated in a greenhouse kept at 30° C. with repeated fertilization and lawn mowing, until the growth of lawn grass became uniform. Immediately after lawn mowing on May 9th, the aqueous dilute liquor of the emulsifiable concentrate of each test compound was applied at a rate of 10 ml/pot by means of a hand sprayer.

On June 2nd, an increase in the height of lawn grass was measured to evaluate the growth controlling effect of the test compound. The effect was expressed in height index with the corresponding increase in the untreated plot as 100. The results are shown in Table 13. It is apparent from the table that the compounds of the present invention have a growth controlling effect on lawn grass.

TABLE 13

| Test compound | Dosage rate (g/a) | Height index (%) |
|---|---|---|
| I-A isomer of Compound 1 | 20 | 71 |
| I-A isomer of Compound 27 | 20 | 74 |
| I-B isomer of Compound 1 | 20 | 86 |
| No treatment | — | 100 (7.0 cm) |

TEST EXAMPLE 12

Herbicidal Activity Test on Paddy Field Weeds

Wagner's pots (1/5,000 are) were each filled with 1.5 kg of paddy field soil and kept under a flooded condition. Rice seedlings in a three-leaf stage were transplanted thereto, and the seeds of barnyard grass (*Echinochloa crus-galli*) and Bulrush sp. (*Scripus juncoides* var. Hotarui Ohwi) were sowed therein. Thereafter, a required amount of each test compound was applied to the soil in a flooded condition.

Twenty-five days after the application, the herbicidal activity of the test compound was examined on the sowed weeds as well as broad-leaf weeds and slender spikerush (*Eleocharis acicularis*) which emerged spontaneously. The results are shown in Table 14.

In applying the test compounds, a pre-determined amount of each compound was formulated into a wettable powder and applied at a rate of 10 cc/pot by means of a pipette. The herbicidal activity was expressed in numerals ranging from 0 to 5.

| 0 | Inhibition percentage | 0–9% |
| 1 | " | 10–29% |
| 2 | " | 30–49% |
| 3 | " | 50–69% |
| 4 | " | 70–89% |
| 5 | " | 90–100% |

All the test compounds did not show phytotoxicity to rice plants, for example malformation, yellowing and chlorosis.

TABLE 14

| Test compound | Dosage rate (g/a) | Barnyard grass | Broad-leaf weed | Bulrush sp. | Slender spikerush |
|---|---|---|---|---|---|
| I-A isomer of Compound 1 | 20 | 5 | 5 | 5 | — |
|  | 10 | 5 | 5 | 5 | — |
| I-A isomer of Compound 3 | 20 | 5 | 5 | 5 | — |
|  | 10 | 4 | 5 | 4 | — |
| I-A isomer of Compound 4 | 20 | 5 | 5 | 5 | — |
|  | 10 | 4 | 5 | 4 | — |
| I-A isomer of Compound 2 | 20 | 5 | 5 | 5 | — |
|  | 10 | 5 | 5 | 5 | — |
| I-A isomer of Compound 27 | 20 | 5 | 5 | 5 | — |
|  | 10 | 5 | 5 | 4 | — |
| I-A isomer of Compound 5 | 20 | 5 | 5 | 5 | — |
|  | 10 | 4 | 5 | 5 | — |
| I-A isomer of Compound 9 | 20 | 5 | 5 | 5 | — |
|  | 10 | 5 | 5 | 5 | — |
| I-B isomer of Compound 1 | 20 | 3 | 3 | 3 | — |
|  | 10 | 2 | 3 | 2 | — |
| I-A isomer of Compound 30 | 40 | 5 | 5 | — | 5 |
| I-B isomer of Compound 30 | 40 | 5 | 5 | — | 5 |
| I-A isomer of Compound 31 | 40 | 5 | 5 | — | 5 |
| I-B isomer of Compound 31 | 40 | 5 | 5 | — | 5 |
| I-A isomer of Compound 32 | 40 | 5 | 5 | — | 5 |
| I-B isomer of Compound 32 | 40 | 5 | 5 | — | 5 |
| I-A isomer of Compound 33 | 40 | 5 | 5 | — | 5 |
| I-B isomer of Compound 33 | 40 | 5 | 5 | — | 5 |
| I-A isomer of Compound 34 | 40 | 5 | 5 | — | 5 |
| I-B isomer of Compound 34 | 40 | 5 | 5 | — | 5 |

TEST EXAMPLE 13

Protective Activity Test on Sheath Blight of Rice (*Rhizoctonia solani*)

The aqueous dilute liquor of the emulsifiable concentrate of each test compound was sprayed on potted rice plants (var.: Kinki No. 33) cultivated in a greenhouse for about 2 months. After air-drying, the leaf sheath of rice stems was inoculated by sticking the mycelial disc (diameter 5 cm) of *Rhizoctonia solani*. After inoculation, the rice plants were infected in a humid chamber (28° C.) for 4 days, and, the plants were observed for the appearance of disease.

The disease severity was calculated as follows: The leaf sheath was measured for a percentage of infected area and classified into the corresponding disease indices, 0, 1, 2, 4, 8; and the disease severity was calculated according to the following equation.

| Disease index | Disease appearance |
|---|---|
| 0 | No infected area and no growth of colony |
| 1 | No infected area but slight growth of colony |
| 2 | Infected area of less than 0.5 cm |
| 4 | Infected area of 0.5-2 cm |
| 8 | Infected area of more than 2 cm |

$$\text{Disease severity (\%)} = \frac{\Sigma(\text{Disease index}) \times (\text{number of leaf sheaths})}{8 \times (\text{Total number of leaf sheaths examined})} \times 100$$

The control of disease was then calculated according to the following equation.

$$\text{Control of disease (\%)} = 100 - \frac{(\text{Disease severity in treated plot})}{(\text{Disease severity in untreated plot})} \times 100$$

As shown in Table 15, it was found that the I-A isomer of the present compounds has a remarkably high protective activity as compared with the I-B isomer, and that the activity is equal or superior to that of the reference compound.

TABLE 15

| | Concentration of active ingredient (ppm) | Control of disease (%) |
|---|---|---|
| Test compound | | |
| I-A isomer of Compound 38 | 500 | 95 |
| I-A isomer of Compound 44 | " | 95 |
| I-A isomer of Compound 45 | " | 95 |
| I-A isomer of Compound 46 | " | 80 |
| I-A isomer of Compound 47 | " | 100 |
| (Reference compound) | | |
| I-B isomer of Compound 38 | " | 0 |
| I-B isomer of Compound 43 | " | 0 |
| I-B isomer of Compound 47 | " | 0 |
| Validamycin *1 | 30 | 78 |

*1 Reference compound (commercial fungicide)

PREPARATION EXAMPLE 1

Dust

One part of the I-A isomer of each of the present compounds (1) to (52), 89 parts of clay and 10 parts of talc are mixed well while being powdered to obtain a dust containing 1% of active ingredient.

PREPARATION EXAMPLE 2

Dust

Three parts of the I-A isomer of each of the present compounds (1) to (52), 67 parts of clay and 30 parts of talc are well mixed while being powdered to obtain a dust containing 3% of active ingredient.

PREPARATION EXAMPLE 3

Wettable Powder

Thirty parts of the I-A isomer of each of the present compounds (1) to (52), 45 parts of diatomaceous earth, 20 parts of white carbon, 3 parts of a wetting agent (sodium laurylsulfate) and 2 parts of a dispersing agent (calcium lignosulfonate) are mixed well while being powdered to obtain a wettable powder containing 30% of active ingredient.

PREPARATION EXAMPLE 4

Wettable Powder

Fifty parts of the I-A isomer of each of the present compounds (1) to (52), 45 parts of diatomaceous earth, 2.5 parts of a wetting agent (calcium alkylbenzenesulfonate) and 2.5 parts of a dispersing agent (calcium lignosulfonate) are well mixed while being powdered to obtain a wettable powder containing 50% of active ingredient.

PREPARATION EXAMPLE 5

Emulsifiable Concentrate

Ten parts of the I-A isomer of each of the present compounds (1) to (52), 80 parts of cyclohexanone and 10 parts of an emulsifier (polyoxyethylene alkylaryl ether) are mixed to obtain an emulsifiable concentrate containing 10% of active ingredient.

PREPARATION EXAMPLE 6

Granule

Five parts by weight of the I-A isomer of each of the present compounds (1) to (52), 40 parts by weight of bentonite, 50 parts by weight of clay and 5 parts by weight of sodium lignosulfonate are mixed well while being powdered. The mixture is kneaded well with water, granulated and dried to obtain a granule.

PREPARATION EXAMPLE 7

Dust

Two parts of the II-A isomer of each of the present compounds (1') to (33'), 88 parts of clay and 10 parts of talc are mixed well while being powdered to obtain a dust containing 2% of active ingredient.

PREPARATION EXAMPLE 8

Dust

Three parts of the II-A isomer of each of the present compound (1') to (33'), 67 parts of clay and 30 parts of talc are mixed well while being powdered to obtain a dust containing 3% of active ingredient.

PREPARATION EXAMPLE 9

Wettable Powder

Thirty parts of the II-A isomer of each of the present compounds (1') to (33'), 45 parts of diatomaceous earth, 20 parts of white carbon, 3 parts of a wetting agent (sodium laurylsulfate) and 2 parts of a dispersing agent (calcium lignosulfonate) are mixed well while being powdered to obtain a wettable powder containing 30% of active ingredient.

PREPARATION EXAMPLE 10

Wettable Powder

Fifty parts of the II-A isomer of each of the present compounds (1') to (33'), 45 parts of diatomaceous earth, 2.5 parts of a wetting agent (calcium alkylbenzenesulfonate) and 2.5 parts of a dispersing agent (calcium lignosulfonate) are mixed well while being powdered to obtain a wettable powder contianing 50% of active ingredient.

PREPARATION EXAMPLE 11

Emulsifiable Concentrate

Ten parts of the II-A isomer of each of the present compounds (1') to (33'), 80 parts of cyclohexanone and 10 parts of an emulsifier (polyoxyethylene alkylaryl ether) are mixed to obtain an emulsifiable concentrate containing 10% of active ingredient.

PREPARATION EXAMPLE 12

Granule

Five parts by weight of the II-A isomer of each of the present compounds (1') to (33'), 80 parts by weight of bentonite, 50 parts by weight of clay and 5 parts by weight of sodium lignosulfonate are mixed well while being powdered. The mixture is kneaded well with water, granulated and dried to obtain a granule containing 5% of active ingredient.

PREPARATION EXAMPLE 13

Wettable Powder

Eighty parts of the I-A isomer of each of the present compounds (1) to (52), 15 parts of diatomaceous earth, 2.5 parts of a wetting agent (calcium alkylbenzenesulfonate) and 2.5 parts of a dispersing agent (calcium lignosulfonate) are mixed well while being powdered to obtain a wettable powder containing 80% of active ingredient.

What is claimed is:

1. One of the two geometrical isomers of a triazole compound represented by the formula,

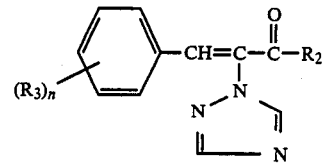

wherein $R_2$ is a $C_1$–$C_6$ alkyl, cyclopropyl or 1-methylcyclopropyl group, $R_3$, which may be the same or different, is a halogen atom, a $C_1$–$C_4$ alkyl, halogen-substituted $C_1$–$C_3$ alkyl, $C_1$–$C_4$ alkoxy, phenoxy, phenyl, cyano or nitro group, and n is an integer of 0 to 3, of which the olefin proton appears at a higher magnetic field on the NMR spectrum in deutero chloroform.

2. One of the two geometrical isomers of a triazole compound represented by the formula,

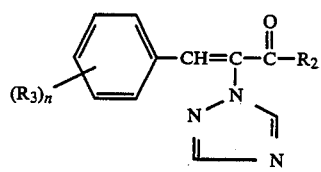

wherein $R_2$ is a 1-methylcyclopropyl group, and $R_3$ and n are as defined in claim 1, of which the olefin proton appears at a lower magnetic field on the NMR spectrum in deutero chloroform.

3. A fungicidal composition for agriculture and horticulture use comprising as an active ingredient a fungicidally effective amount of one of the two geometrical isomers of a triazole compound of the formula,

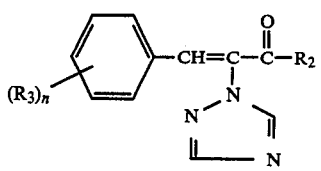

wherein $R_2$, $R_3$ and n are as defined in claim 1 and in which the olefin proton appears at a higher magnetic field on the NMR spectrum in deutero chloroform, or salts thereof and an agriculturally or horticulturally acceptable carrier.

* * * * *